United States Patent
Bovy et al.

(10) Patent No.: US 7,453,010 B2
(45) Date of Patent: Nov. 18, 2008

(54) PHENYLCYCLOHEXYLPROPANOLAMINE DERIVATIVES, PREPARATION AND THERAPEUTIC APPLICATION THEREOF

(75) Inventors: Philippe R. Bovy, Mareil Marly (FR); Roberto Cecchi, Lodi (IT); Tiziano Croci, Milan (IT); Olivier Venier, Saint Mande (FR)

(73) Assignee: Sanofi Aventis, Paris (FR)

( * ) Notice: Subject to any disclaimer, the term of this patent is extended or adjusted under 35 U.S.C. 154(b) by 368 days.

(21) Appl. No.: 10/515,145

(22) PCT Filed: May 26, 2003

(86) PCT No.: PCT/FR03/01580

§ 371 (c)(1),
(2), (4) Date: Aug. 30, 2005

(87) PCT Pub. No.: WO03/099772

PCT Pub. Date: Dec. 4, 2003

(65) Prior Publication Data

US 2006/0100283 A1    May 11, 2006

(30) Foreign Application Priority Data

May 29, 2002    (FR) .................................. 02 06561

(51) Int. Cl.
*C07C 311/00*    (2006.01)
*A61K 31/18*    (2006.01)
(52) U.S. Cl. ........................... 564/98; 564/99; 564/399; 562/429; 560/12; 560/13; 549/445; 548/491; 514/464; 514/415; 514/538; 514/562; 514/605
(58) Field of Classification Search .................... None
See application file for complete search history.

(56) References Cited

U.S. PATENT DOCUMENTS 4,004,028 A    1/1977    Kaiser

OTHER PUBLICATIONS

Derwent Patent Abstract No. 200248 (2004).
Derwent Patent Abstract No. 200011 (2004).

*Primary Examiner*—Brian J Davis
(74) *Attorney, Agent, or Firm*—Jianq Lin

(57) ABSTRACT

The invention relates to compounds of general formula (I):

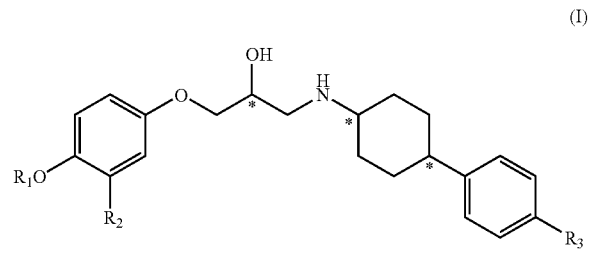

where $R_1$ represents H or a $(C_1-C_4)$alkyl, —$CO(C_1-C_4)$alkyl, $(C_1-C_4)$alkylphenyl or —CO-phenyl group, said phenyl optionally being substituted; $R_2$ represents H, a halogen atom, an —$S(O)_z(C_1-C_4)$alkyl group, where z is equal to 0, 1 or 2, an —$NHSO_2(C_1-C_4)$alkyl group, an —$NHSO_2$-phenyl group or an —$NHSO_2$—$(C_1-C_4)$alkylphenyl group, said phenyl optionally being substituted; $R_3$ represents an —X—$R_4$ group—in which X represents a bond, an oxygen atom or a —$CH_2$— group and $R_4$ represents H or a —$CR_5R_6$—$COOR_7$ group, where $R_5$, $R_6$ and $R_7$ independently represent H or a $(C_1-C_4)$alkyl group—a phenyl group optionally substituted or fused with a dioxolane group, a —CO—$NR_8R_9$ group—where $R_8$ represents H, a $(C_1-C_4)$alkyl group or a $(C_1-C_4)$alkyl$(C_1-C_4)$alkoxy group and $R_9$ represents a $(C_1-C_4)$alkyl$(C_1-C_4)$alkoxy group, a —$(CH_2)_n$-A group, where n is equal to 0, 1, 2, 3 or 4 and where A represents an indolyl group, a fluorenyl group or a phenyl group which is substituted, an optionally substituted —NH-phenyl group or a —$CH(R_{10})$—$(CH_2)_n$—$COOR_{11}$ group, where n is 0, 1, 2 or 3 and where $R_{11}$ represents H or a $(C_1-C_4)$alkyl group and $R_{10}$ represents H, a $(C_1-C_4)$alkyl group or a —$CH_2$-phenyl group, said phenyl optionally being substituted, or a —$COOR_{12}$ group, where $R_{12}$ represents H or a $(C_1-C_4)$alkyl group; their process of preparation and their therapeutic application.

34 Claims, No Drawings

PHENYLCYCLOHEXYLPROPANOLAMINE DERIVATIVES, PREPARATION AND THERAPEUTIC APPLICATION THEREOF

This application is a 371 of PCT/FR03/01580 filed May 26, 2003.

The present invention relates to phenylcyclohexylpropanolamine derivatives, to their preparation and to their therapeutic application.

A subject-matter of the present invention is compounds corresponding to the formula (I)

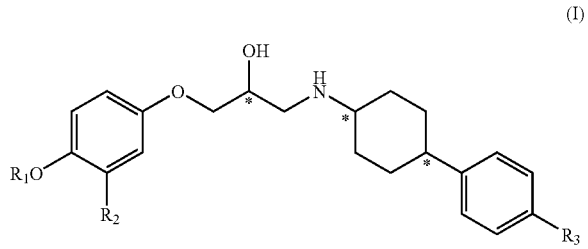

in which:

$R_1$ represents a hydrogen atom or a $(C_1-C_4)$alkyl group, a —$CO(C_1-C_4)$alkyl group, a $(C_1-C_4)$alkylphenyl group or a —CO-phenyl group, said phenyl optionally being substituted by one to three groups chosen, independently of one another, from halogen atoms, $(C_1-C_4)$alkyl groups and $(C_1-C_4)$alkoxy groups;

$R_2$ is chosen from one of the following groups:
a hydrogen atom,
a halogen atom,
an —$S(O)_z(C_1-C_4)$alkyl group, where z is equal to 0, 1 or 2,
an —$NHSO_2(C_1-C_4)$alkyl group,
an —$NHSO_2$-phenyl group, or
an —$NHSO_2$—$(C_1-C_4)$alkylphenyl group,
where said phenyl is optionally substituted by one to three groups chosen, independently of one another, from halogen atoms, $(C_1-C_4)$alkyl groups and $(C_1-C_4)$alkoxy groups; and $R_3$ is chosen from one of the following groups:
an —X—$R_4$ group, in which X represents a bond, an oxygen atom or a —$CH_2$— group and $R_4$ represents a hydrogen atom or a group of formula —$CR_5R_6$—$COOR_7$, where $R_5$, $R_6$ and $R_7$ represent, independently of one another, a hydrogen atom or a $(C_1-C_4)$alkyl group, $R_4$ not representing, however, a hydrogen atom when X represents a bond,
a phenyl group optionally substituted by one to three groups chosen, independently of one another, from halogen atoms, $(C_1-C_4)$alkyl groups and $(C_1-C_4)$alkoxy groups or fused with a dioxolane group (so as to form a benzodioxolane group), or
a —CO—$NR_8R_9$ group, in which $R_8$ represents a hydrogen atom, a $(C_1-C_4)$alkyl group or a $(C_1-C_4)$alkyl$(C_1-C_4)$alkoxy group and $R_9$ is chosen from one of the following groups:
a $(C_1-C_4)$alkyl$(C_1-C_4)$alkoxy group,
a group of formula —$(CH_2)_n$-A, where n is equal to 0, 1, 2, 3 or 4 and where A represents an indolyl, fluorenyl or phenyl group, where the phenyl group is substituted by one to three groups chosen, independently of one another, from halogen atoms, hydroxyl groups and $(C_1-C_4)$alkyl groups,
an —NH-phenyl group, where the phenyl group is optionally substituted by one to three groups chosen, independently of one another, from halogen atoms, hydroxyl groups and $(C_1-C_4)$alkyl groups, or
a group of formula —$CH(R_{10})$—$(CH_2)_n$—$COOR_{11}$, where n is equal to 0, 1, 2 or 3, $R_{11}$ represents a hydrogen atom or a $(C_1-C_4)$alkyl group and $R_{10}$ represents:
a hydrogen atom,
a $(C_1-C_4)$alkyl group,
a —$COOR_{12}$ group, where $R_{12}$ represents a hydrogen atom or a $(C_1-C_4)$alkyl group or
a —$CH_2$-phenyl group, where the phenyl group is optionally substituted by one to three groups chosen, independently of one another, from halogen atoms, hydroxyl groups and $(C_1-C_4)$alkyl groups.

The compounds of formula (I) can comprise one or more asymmetric carbon atoms. Furthermore, the cyclohexyl group of these compounds exhibits a geometrical asymmetry. The * symbols in the above formula (I) denote the carbons which can give rise to different geometrical configurations.

The compounds of formula (I) can thus exist in the form of enantiomers or of diastereoisomers. These enantiomers, diastereoisomers and their mixtures, including racemic mixtures, form part of the invention.

Preference is given in particular to the compounds of formula (I) according to the invention which exhibit the following configuration:

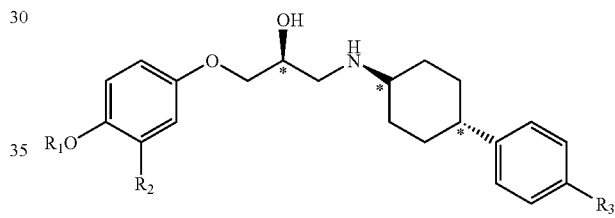

The compounds of formula (I) can exist in the form of bases or of addition salts with acids. Such addition salts form part of the invention.

These salts are advantageously prepared with pharmaceutically acceptable acids but the salts of other acids, for example of use for the purification or the isolation of the compounds of formula (I) also form part of the invention.

The compounds of formula (I) can also exist in the form of hydrates or solvates, namely in the form of combinations or associations with one or more molecules of water or with a solvent. Such hydrates and solvates also form part of the invention.

In the context of the present invention:
the term "a halogen atom" is understood to mean: a fluorine, a chlorine, a bromine or an iodine;
the term "a $(C_1-C_4)$alkyl group" is understood to mean: a linear or branched, saturated aliphatic group comprising from 1 to 4 carbon atoms (it being clearly understood that such a group can be only linear when it comprises less than 3 carbon atoms and that such a group can be linear or branched when it comprises 3 or 4 carbon atoms). Mention may be made, by way of examples, of the methyl, ethyl, propyl, isopropyl, butyl or isobutyl groups, and the like;
the term "a $(C_1-C_4)$alkoxy group" is understood to mean: an —O—$(C_1-C_4)$alkyl radical, where the $(C_1-C_4)$alkyl group is as defined above;

the term "a $(C_1-C_4)$alkyl$(C_1-C_4)$alkoxy group" is understood to mean: a radical of formula $(C_1-C_4)$alkyl-O—$(C_1-C_4)$alkyl, where the $(C_1-C_4)$alkyl group is as defined above; and the term "a $(C_1-C_4)$alkylphenyl group" is understood to mean: a group of formula —$(CH_2)_x$-phenyl, where x is between 1 and 4.

Mention may be made, among the compounds of formula (I) which are subject matters of the invention, of the preferred compounds in which $R_1$ represents a hydrogen atom and/or $R_2$ represents an —$SO_2(C_1-C_4)$alkyl group (such as an —$SO_2CH_3$ group) or an —$NHSO_2(C_1-C_4)$alkyl group (such as an —$NHSO_2CH_3$ group).

Preference is also given, among the compounds of formula (I) which are subject matters of the invention, to those in which $R_1$ represents a hydrogen atom;

and/or $R_2$ represents an —$SO_2(C_1-C_4)$alkyl group (such as an —$SO_2CH_3$ group) or an —$NHSO_2(C_1-C_4)$alkyl group (such as an —$NHSO_2CH_3$ group);

and/or $R_3$ is chosen from one of the following groups:
an —X—$R_4$ group, in which X represents a bond, an oxygen atom or a —$CH_2$— group and $R_4$ represents a hydrogen atom or a group of formula —$CR_5R_6$—$COOR_7$, where $R_5$, $R_6$ and $R_7$ are as defined above, $R_4$ not representing, however, a hydrogen atom when X represents a bond or a —$CH_2$— group, a phenyl group optionally substituted by one to three groups chosen, independently of one another, from halogen atoms, $(C_1-C_4)$alkyl groups and $(C_1-C_4)$alkoxy groups or fused with a dioxolane group, or a —CO—$NR_8R_9$ group, in which $R_8$ is as defined above and $R_9$ is chosen from one of the following groups:

a $(C_1-C_4)$alkyl$(C_1-C_4)$alkoxy group, a group of formula —$(CH_2)_n$-A, where n is equal to 0, 1, 2, 3 or 4 and where A represents an indolyl group, a fluorenyl group or a phenyl group substituted by one to three groups independently chosen from halogen atoms, hydroxyl groups and $(C_1-C_4)$alkyl groups, an —NH-phenyl group, where the phenyl group is optionally substituted by one to three groups chosen, independently of one another, from halogen atoms, hydroxyl groups and $(C_1-C_4)$alkyl groups, or a group of formula —$CH(R_{10})$—$(CH_2)_n$—$COOR_{11}$, where n is equal to 0, 1, 2 or 3, $R_{11}$ represents a hydrogen atom or a $(C_1-C_4)$alkyl group and $R_{10}$ represents:
a hydrogen atom,
a $(C_1-C_4)$alkyl group,
a —$COOR_{12}$ group, where $R_{12}$ represents a hydrogen atom or a $(C_1-C_4)$alkyl group, or
a —$CH_2$-phenyl group, where the phenyl group is optionally substituted by one to three groups chosen, independently of one another, from halogen atoms, hydroxyl groups and $(C_1-C_4)$alkyl groups.

Mention may also be made of the preferred compounds of formula (I) in which:

$R_1$ represents a hydrogen atom;

and/or $R_2$ represents an —$SO_2(C_1-C_4)$alkyl group (such as an —$SO_2CH_3$ group) or an —$NHSO_2(C_1-C_4)$alkyl group (such as an —$NHSO_2CH_3$ group);

and/or $R_3$ represents a —CO—$NHR_9$ group, in which $R_9$ is chosen from one of the following groups:

a group of formula —$(CH_2)_n$-A, where n is equal to 0, 1, 2, 3 or 4 and where A represents an indolyl group, a fluorenyl group or a phenyl group substituted by one to three groups independently chosen from halogen atoms, hydroxyl groups and $(C_1-C_4)$alkyl groups, an —NH-phenyl group, where the phenyl group is optionally substituted by one to three groups chosen, independently of one another, from halogen atoms, hydroxyl groups and $(C_1-C_4)$alkyl groups, or a group of formula —$CH(R_{10})$—$(CH_2)_n$—$COOR_{11}$, where n is equal to 0, 1, 2 or 3, $R_{11}$ represents a hydrogen atom or a $(C_1-C_4)$alkyl group and $R_{10}$ represents:
a hydrogen atom,
a $(C_1-C_4)$alkyl group,
a —$COOR_{12}$ group, where $R_{12}$ represents a hydrogen atom or a $(C_1-C_4)$alkyl group, or
a —$CH_2$-phenyl group, where the phenyl group is optionally substituted by one to three groups chosen, independently of one another, from halogen atoms, hydroxyl groups and $(C_1-C_4)$alkyl groups.

In what follows, the term "protective group Pg" is understood to mean a group which makes it possible, first, to protect a reactive functional group, such as a hydroxyl or an amine, during a synthesis and, secondly, to regenerate the reactive functional group intact at the end of the synthesis. Examples of protective groups and methods for protecting and deprotecting are given in "Protective Groups in Organic Synthesis", Green et al., 2nd edition (John Wiley & Sons Inc. New York).

In accordance with the invention, the compounds of general formula (I), where $R_3$ is other than a —CO—$NR_8R_9$ group (that is to say, where $R_3$ represents an —X—$R_4$ group or a phenyl group optionally substituted or fused with one or more other groups, as defined above), can be prepared according to the process described in scheme 1.

Scheme 1:

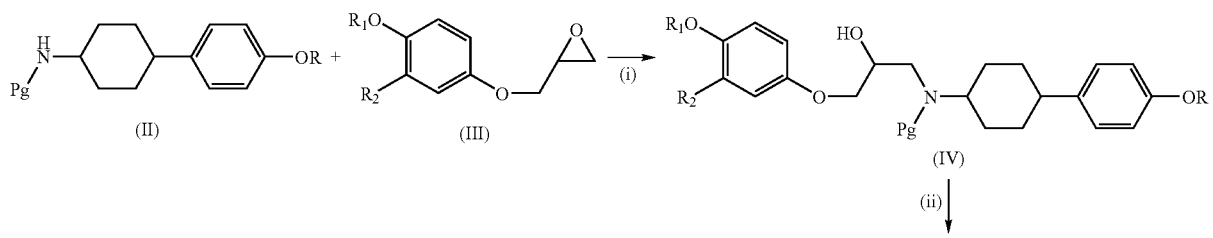

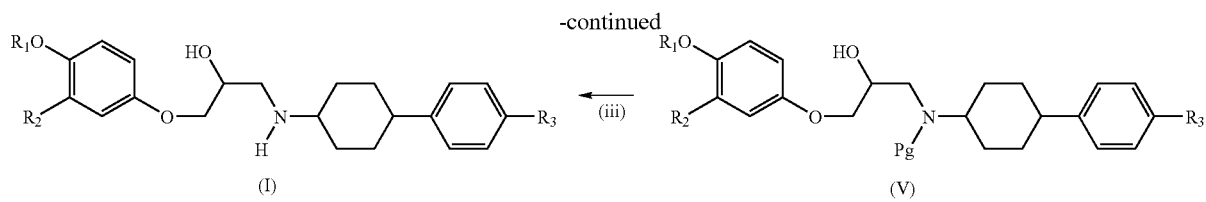

According to scheme 1, in a stage (i), the compound of formula (II), where Pg represents a protective group and R represents an electrophilic group, is reacted with the epoxide of formula (III), where $R_1$ and $R_2$ are as defined above.

The compounds of formula (III) are known in the literature (for example in the patent application published under the number WO 02/44139) or else can be prepared by processes analogous to the processes which are described therein. In the case where $R_2$ can react during this stage (i) or the subsequent stages, it is protected beforehand using protective groups well known to a person skilled in the art. Furthermore, when $R_1$ represents a hydrogen atom, it is preferable to protect the hydroxyl functional group by a protective group in order to increase the yield of the reaction. To this end, use may be made of standard protective groups for phenol groups, such as methoxyethoxymethyl (MEM), trimethylsilylethoxymethyl (SEM), benzyl, which is optionally substituted, or benzoyl.

With regard to the amine of the compound (II), it is partially protected using a protective group Pg, such as an optionally substituted benzyl group (for example a para-methoxybenzyl group) or a methoxyethoxymethyl (MEM) group. It is preferable here to use protective groups which only partially protect the reactivity of the amine functional group, that is to say which do not detrimentally affect its nucleophilic nature. During stage (i), the partially protected primary amine in the compound (II) can react only with a single molecule of the epoxide (III) and not with two molecules, thus preventing the formation of reaction by-products. Stage (i) results in the aminoalcohol of formula (IV). This stage is, for example, carried out in an organic solvent, such as a lower alcohol, for example methanol, ethanol, isopropanol or tert-butanol, or also in dimethyl sulfoxide, in a linear or cyclic ether, in an amide, such as dimethylformamide or dimethylacetamide, or also in a mixture of these solvents, preferably using at least equimolar amounts of the reactants. The temperature of the reaction is advantageously between ambient temperature and the reflux temperature of the solvent chosen.

In a stage (ii), the OR group is converted to an $R_3$ functional group, $R_3$ being as defined above but being other than a —CO—$NR_8R_9$ group. For example, in the case where the OR group represents a triflate functional group, a coupling can be carried out with an arylboronic or aryltin derivative with catalysis by a transition metal, such as palladium, in the presence of a phosphine, in a solvent, such as toluene, tetrahydrofuran, DME or dimethylformamide, and if necessary in the presence of a base (for example sodium carbonate) and of water; a compound (V) is then obtained where $R_3$ is an aryl group, for example a phenyl group optionally substituted or fused with one or more other groups as defined in the formula (I) of the compounds according to the invention.

In the case where OR represents an —O—$CR_5R_6$—$COOR_7$ group, where $R_5$ and $R_6$ are as defined in the formula (I) and $R_7$ represents a $(C_1$-$C_4)$alkyl group, it is possible, during stage (ii), to hydrolyze the ester functional group to an acid, in order to obtain a compound (V) in which $R_3$=—O—$CR_5R_6$—COOH, by treatment with a base, for example sodium hydroxide, in a solvent or a mixture of solvents, such as an ethanol/water mixture.

It is clearly understood that, when the OR group in the starting compound (II) already represents the desired $R_3$ group, then stage (ii) has no reason to occur. For example, when OR represents a hydroxyl group, then the desired compound (V) in which $R_3$=OH is obtained directly by reaction between the compounds (II) and (III).

The compounds of formula (I) are finally obtained in a stage (iii) after removal of the protective groups using techniques known to a person skilled in the art. In particular, when the protective groups are benzyl groups, deprotection is carried out using hydrogen in the presence of palladium-on-charcoal in a solvent, such as ethanol. However, in the case where $R_2$ represents an —$S(O)(C_1$-$C_4)$alkyl group, this stage of removal of the protective groups will preferably be avoided and use will preferably be made, as starting material, of a compound (II) carrying a primary amine (Pg=H for the compounds (II), (IV) and (V) in scheme 1).

The compounds of formula (II), used as starting materials in the process according to scheme 1, can be prepared according to the process presented in scheme 2.

Scheme 2:

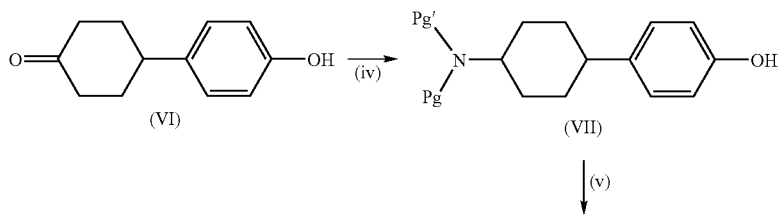

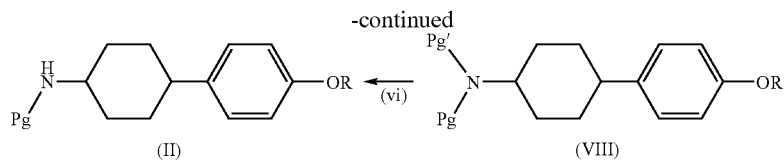

In scheme 2, the ketone functional group of the compound of formula (VI) is converted, in a stage (iv), to an amine functional group according to methods well known to a person skilled in the art (for example by reductive amination). This amine is protected using two protective groups Pg and Pg'. Pg and Pg' have different chemical natures, in particular with regard to their method of deprotection (which subsequently makes possible selective deprotection of one or other of the protective groups). For example, Pg can be a benzyl group and Pg' a carbamate functional group. Pg and Pg' are introduced according to methods well known to a person skilled in the art (for example by addition of an acid anhydride or acid chloride for the introduction of a carbamate unit) and generally after the conversion of the ketone functional group of the compound (VI) to an amine functional group.

During stage (v), the compound (VIII) is obtained by reacting the phenol functional group of the compound (VII) with an electrophile (R group) which can be an acid anhydride, an acid halide or a halogenated alkyl derivative. When an acid halide or an acid anhydride (for example trifluoromethanesulfonic anhydride) is reacted, the reaction is carried out in a solvent, such as tetrahydrofuran, a linear ether, dichloromethane or toluene, and in the presence of a base, such as triethylamine, pyridine or diisopropylethylamine. In the case where a halogenated alkyl derivative (for example ethyl bromoacetate) is reacted, the reaction is carried out in a solvent, such as tetrahydrofuran, acetone or dimethylformamide, and in the presence of a base, such as sodium hydride, potassium bicarbonate or sodium hydroxide.

The compound (II) is obtained, in the final stage (vi), by selective deprotection of the protective group Pg' from the cyclohexylamine (VIII) according to methods well known to a person skilled in the art. For example, in the case where Pg is a benzyl group and Pg' is a tert-butoxycarbonyl group, deprotection is carried out using a solution of trifluoroacetic acid in dichloromethane.

Furthermore, the compounds of general formula (I), where $R_3$ represents a —CO—$NR_8R_9$ group ($R_8$ and $R_9$ being as defined above in connection with the formula (I) of the compounds according to the invention), can be prepared according to the process described in scheme 3.

Scheme 3:

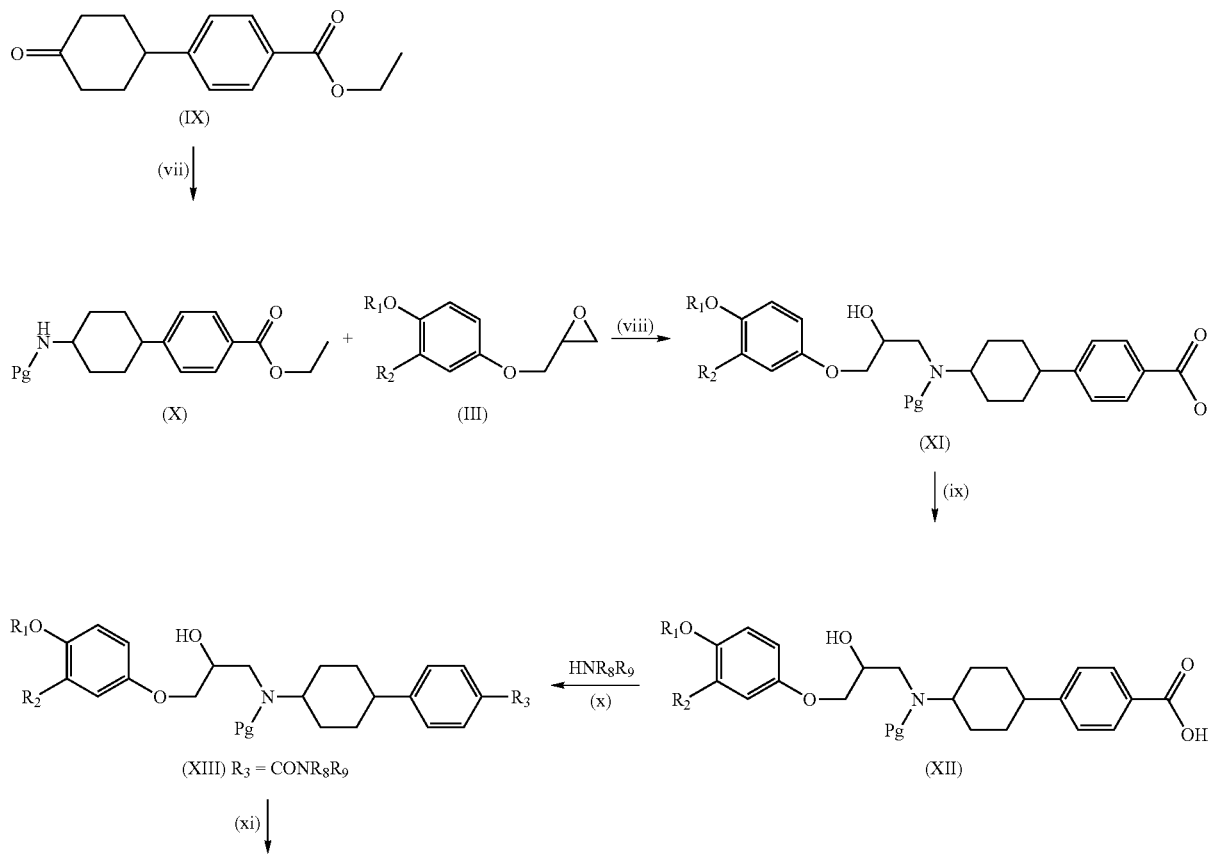

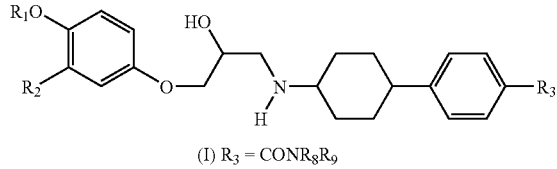

(I) R₃ = CONR₈R₉

According to scheme 3, the ketone functional group of the compound of formula (IX) is converted, in a stage (vii), to an amine group according to methods well known to a person skilled in the art (for example by reductive amination). The amine (X) is partially protected using a protective group Pg, such as an optionally substituted benzyl group (for example a para-methoxybenzyl group) or a methoxyethoxymethyl (MEM) group. It is preferable here to use protective groups which only partially protect the reactivity of the amine functional group, that is to say which do not detrimentally affect its nucleophilic nature. However, in the case where $R_2$ represents an —S(O)($C_1$-$C_4$)alkyl group, use will preferably be made of a compound (X) carrying a primary amine (Pg=H for the compound (X) in scheme 3).

In a stage (viii), the compound of formula (X) is reacted with the epoxide of formula (III) already defined in scheme 1 above. In the case where $R_2$ represents an —S(O)($C_1$-$C_4$) alkyl group, the nitrogen of the compound (XI) will subsequently be protected with an amino-protective group, such as t-butyloxycarbonyl (BOC) (Pg=BOC in scheme 3 for the compounds (XI), (XII) and (XIII)), according to methods known to a person skilled in the art. In the case where $R_2$ can react during this stage (viii) or the subsequent stages, it is protected beforehand using protective groups well known to a person skilled in the art. Furthermore, when $R_1$ represents a hydrogen atom, it is preferable to protect the hydroxyl functional group by a protective group in order to increase the yield of the reaction, as explained above in connection with scheme 1.

During stage (viii), the partially protected primary amine in the compound (X) can react only with a single molecule of the epoxide (III) and not with two molecules, thus preventing the formation of reaction by-products.

Stage (viii) results in the aminoalcohol of formula (XI). This stage is carried out, for example, in an organic solvent, such as a lower alcohol, for example methanol, ethanol, isopropanol or tert-butanol, or also in dimethyl sulfoxide, in a linear or cyclic ether, in an amide, such as dimethylformamide or dimethylacetamide, or also in a mixture of these solvents, preferably using at least equimolar amounts of the reactants. The temperature of the reaction is advantageously between ambient temperature and the reflux temperature of the solvent chosen.

In a stage (ix), the ethyl ester of the compound (XI) is hydrolyzed to an acid (XII) by treatment by a base, for example sodium hydroxide, in a solvent or a mixture of solvents, such as an ethanol/water mixture.

The amide of formula (XIII) is obtained, in a stage (x), by reacting the acid (XII) with an amine of formula $HNR_8R_9$, in which $R_8$ and $R_9$ are as defined in connection with the formula (I) described above, in the presence of a coupling agent, for example 1-ethyl-3-(3-dimethylaminopropyl)carbodiimide (EDC), benzotriazol-1-yloxytris(dimethylamino)phosphonium hexafluorophosphate (BOP) or benzotriazol-1-yloxy-N,N'-tetramethyluronium tetrafluoroborate (TBTU), and in the presence of a base, such as triethylamine or pyridine, in a solvent, such as dichloromethane, acetonitrile or chloroform. It is also possible to activate the acid functional group of the compound (XII) in the form of an acid chloride or of a carbonic anhydride according to techniques known to a person skilled in the art.

The compounds of formula (I) are finally obtained, in a stage (xi), after removal of the protective groups using techniques known to a person skilled in the art or, if necessary, after conversion of an ester group to an acid functional group and then removal of the protective groups. In particular, when the protective groups are benzyl groups, deprotection is carried out by means of hydrogen in the presence of palladium-on-charcoal in a solvent, such as ethanol.

In the case where the compound (XIII) comprises, as $R_9$ group, an ester group of formula —CH($R_{10}$)—($CH_2$)$_n$—COOR$_{11}$, where $R_{11}$ represents a ($C_1$-$C_4$)alkyl group and $R_{10}$ is as defined above in connection with the compounds of formula (I) in accordance with the invention, then the stage of removal of the protective groups is carried out after conversion of the ester group to an acid functional group.

In scheme 3, it is clearly understood that it is possible to use, as starting material (IX), an ester other than an ethyl ester, for example a methyl or propyl ester or any other ester of a lower alkyl.

The compounds of formula (IX), of use in the implementation of the process presented in scheme 3, can be prepared according to scheme 4, illustrated by way of example for the preparation of an ethyl ester as compound (IX)

Scheme 4:

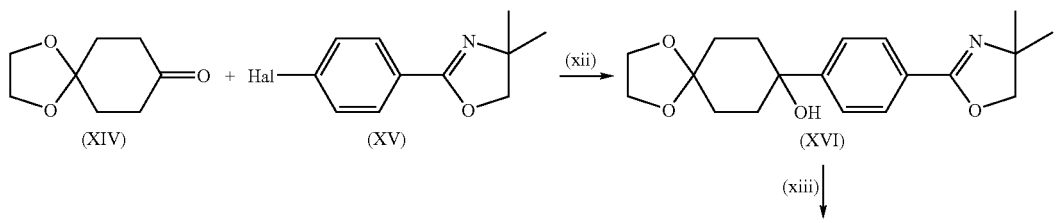

(XIV)    (XV)    (XVI)

(xiii)

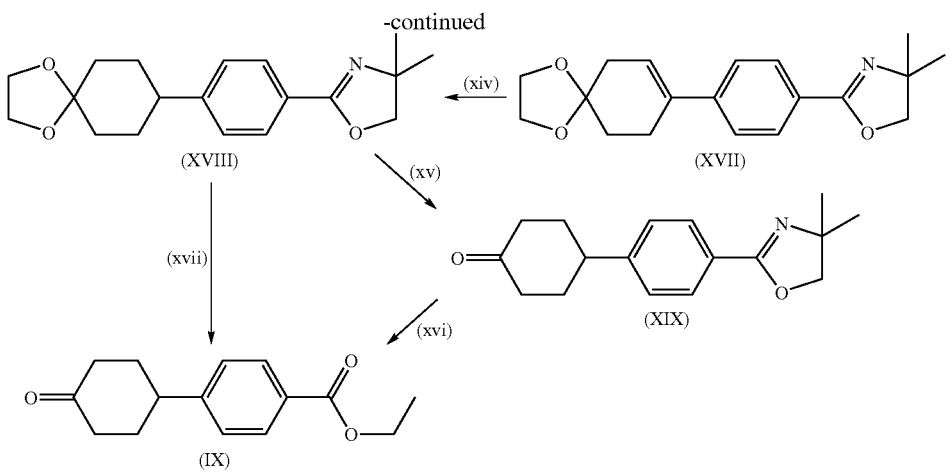

According to scheme 4, in a stage (xii), the compound of formula (XIV) is condensed with the compound of formula (XV), in which Hal represents a halogen atom, preferably bromine, for example according to the method described by Meyers et al. in J. Org. Chem., 1974, 39, 2787. The intermediate alcohol of formula (XVI) thus obtained is converted, in a stage (xiii), to an unsaturated compound (XVII), for example using $SOCl_2$ in pyridine, according to the method described by Gonzales-Cameno et al. in Tetrahedron, 1994, 50, 10971, or else using $POCl_3$, as described, for example, in Org. Prep. Proced. Int., 1995, 27, 122.

The unsaturated compound (XVII) is subsequently reduced, in a stage (xiv), to a compound (XVIII) according to conventional methods, for example using hydrogen in the presence of palladium-on-charcoal in a solvent, such as ethanol.

The acetal group of the compound (XVIII) is hydrolyzed, in a stage (xv), analogously to the reaction described by Szantay et al. in Tetrahedron, 1996, 52(33), 11053, namely using hydrochloric acid in acetone, and results in the compound (XIX), which is subsequently hydrolyzed to a compound (IX), in a stage (xvi), according to the method described by Seebach et al. in Synthesis Communications, 1982, 138, or by Nelson et al. in J. Org. Chem., 1994, 59(9), 2577. Alternatively, the compound (XVIII) can be converted directly to the compound (IX) by heating at reflux in ethanol and addition of sulfuric acid, according to the method described by Degraw et al. in J. Med. Chem., 1992, 35(2), 320, or by Taylor et al. in Heterocycles, 1996, 43(2), 323.

It is clearly understood that a process identical to that presented in scheme 4 could be employed for the preparation of compounds (IX) in the form of esters other than the ethyl ester by hydrolyzing the compound (XVIII) using alcohols carrying alkyl groups other than an ethyl group.

In schemes 1, 2, 3 and 4, the starting compounds and the reactants, when their method of preparation is not described, are available commercially or are described in the literature or else can be prepared according to methods which are described therein or which are known to a person skilled in the art.

The following examples describe the preparation of some compounds in accordance with the invention. These examples are not limiting and only illustrate the present invention. The numbers of the compounds given in the examples refer to those given in the table below, in which the chemical structures and the physical properties of a few compounds according to the invention are illustrated.

Preparation 1: trans-4{4-[Benzyl((2S)-3-{4-(benzyloxy)-3-[(methylsulfonyl)amino]phenoxy}-2-hydroxypropyl)amino]cyclohexyl}phenyl trifluoromethanesulfonate (Intermediate product of formula (IV) where $R_1$=Pg=benzyl, $R_2$=—NH—$SO_2$—$CH_3$ and R=—$SO_2CF_3$)

1.1: trans-4-[4-(Benzylamino)cyclohexyl]phenol hydrochloride

A solution of 12.2 ml of benzylamine (111 mmol) and of 5.3 g of 4-(4'-hydroxyphenyl)cyclohexanone (27 mmol) in trimethyl orthoformate (100 ml) is heated at 50° C. for 3 h. The solvents are evaporated under reduced pressure and 100 ml of isopropanol and then 1.16 g of sodium borohydride are added. The reaction mixture is left stirring for 16 h. The solvents are evaporated under reduced pressure and a molar aqueous hydrochloric acid solution is added to pH=1. The precipitate is filtered off and washed under hot conditions with acetonitrile. trans-4-[4-(Benzylamino)cyclohexyl]phenol hydrochloride is obtained in the form of a solid (4 g, 48%). [M+H$^+$]=282.5

1.2: tert-Butyl trans-benzyl[4-(4-hydroxyphenyl) cyclohexyl]carbamate

A solution of 13.7 g of trans-4-[4-(benzyl-amino)cyclohexyl]phenol hydrochloride (48.7 mmol) and of 11.69 g of di(tert-butyl) dicarbonate (53.3 mmol) in ethyl acetate (295 ml) is heated at reflux for 4 h. The solvents are subsequently evaporated under reduced pressure and the tert-butyl trans-benzyl[4-(4-hydroxyphenyl)cyclohexyl]carbamate is obtained in the form of crystals (12.68 g, 68.2%) after purification on silica gel (eluent: dichloromethane/methanol 98/2). [M+H$^+$]=382.4

1.3: trans-4-{4-[Benzyl(tert-butoxycarbonyl)amino] cyclohexyl}phenyl trifluoromethanesulfonate A solution of 12.6 g of tert-butyl trans-benzyl[4-(4-hydroxyphenyl)cyclohexyl]carbamate (33 mmol) and of 11.5 ml of 2,6-lutidine (99 mmol) in dichloromethane (125 ml) is stirred at 0° C. 6.1 ml of trifluoromethanesulfonic anhydride are subsequently added and the reaction mixture is left stirring for 1 h 30. Water is added and the aqueous phase is extracted once with dichloromethane. The organic phases are combined and dried over sodium sulfate. The solvents are evaporated under reduced pressure and trans-4-{4-[benzyl(tert-butoxycarbonyl)amino]cyclohexyl}phenyl trifluoromethanesulfonate is obtained in the form of crystals (16.43 g, 97%) after purification on silica gel (eluent: dichloromethane). [M+H$^+$]=514.4

1.4: trans-4-[4-(Benzylamino)cyclohexyl]phenyl trifluoromethanesulfonate

A solution of 16.4 g of trans-4-{4-[benzyl(tert-butoxycarbonyl)amino]cyclohexyl}phenyl trifluoromethanesulfonate (32 mmol) in a mixture of trifluoroacetic acid (150 ml) and dichloromethane (900 ml) is stirred for 1 h 30. The solvents are evaporated under reduced pressure and then water, ethyl acetate and an aqueous ammonia solution are added. The organic phase is washed once with water and dried over sodium sulfate. trans-4-[4-(Benzylamino)cyclohexyl]-phenyl trifluoromethanesulfonate is obtained in the form of crystals (12.96 g, 98%) after evaporation of the solvents under reduced pressure. [M+H$^+$]=414.2

1.5: trans-4-{4-[Benzyl((2S)-3-{4-(benzyloxy)-3-[(tert-butoxycarbonyl)(methylsulfonyl)amino]phenoxy}-2-hydroxypropyl)amino]cyclohexyl}phenyl trifluoromethanesulfonate A mixture of 5.52 g of trans-4-[4-(benzylamino)cyclohexyl]phenyl trifluoromethanesulfonate (13.3 mmol) and of 5 g of 4-benzyloxy-3-(N-(tert-butoxycarbonyl)-N-(methylsulfonyl)amino)-1-((2S)-2,3-epoxypropoxy)benzene (11.2 mmol) in ethanol (72 ml) is brought to reflux for 5 h. The solvent is evaporated under reduced pressure and trans-4-{4-[benzyl((2S)-3-{4-(benzyloxy)-3-[(tert-butoxycarbonyl)(methylsulfonyl)amino]phenoxy}-2-hydroxypropyl)amino]cyclohexyl}phenyl trifluoromethanesulfonate is obtained in the form of an oil (6.94 g, 72%) after purification on silica gel (eluent: dichloromethane/methanol 98/2). [M+H$^+$]=863.4

1.6: trans-4-{4-[Benzyl((2S)-3-{4-(benzyloxy)-3-[(methylsulfonyl)amino]phenoxy}-2-hydroxypropyl)amino]cyclohexyl}phenyl trifluoromethanesulfonate A solution of 1.4 g of trans-4-{4-[benzyl((2S)-3-{4-(benzyloxy)-3-[(tert-butoxycarbonyl)(methylsulfonyl)amino]phenoxy)-2-hydroxy-propyl)amino]cyclohexyl}phenyl trifluoromethanesulfonate (1.62 mmol) in a mixture of trifluoroacetic acid (5 ml) and of dichloromethane (45 mol) is stirred for 3 h 20. The solvents are evaporated under reduced pressure and then water, ethyl acetate and an aqueous ammonium solution are added. The organic phase is washed once with water and dried over sodium sulfate. trans-4-{4-[Benzyl((2S)-3-{4-(benzyloxy)-3-[(methylsulfonyl)amino]phenoxy}-2-hydroxypropyl)amino]cyclohexyl}phenyl trifluoromethanesulfonate is obtained in the form of an oil (1.27 g, 98%) after evaporation of the solvents under reduced pressure. [M+H$^+$]=763.5.

Preparation 2: Ethyl trans-(4-{4-[benzyl((2S)-3-{4-(benzyloxy)-3-[(methylsulfonyl)amino]phenoxy}-2-hydroxypropyl)amino]cyclohexyl}-phenoxy)acetate (Intermediate product of formula (IV) where $R_1$=Pg=benzyl, $R_2$=—NH—SO$_2$—CH$_3$ and R=—CH$_2$COOEt)

2.1: Ethyl trans-(4-{4-[benzyl(tert-butoxycarbonyl)amino]cyclohexyl}phenoxy)acetate A suspension of 3.82 g (10 mmol) of tert-butyl trans-benzyl[4-(4-hydroxyphenyl)-cyclohexyl]carbamate (cf. preparation 1.2) and of 0.48 g of 60% sodium hydride (12 mmol) in dimethylformamide (38 ml) is stirred for 25 minutes and then 1.44 ml of ethyl bromoacetate (13 mmol) are added. The reaction is left stirring for 4 h. The reaction medium is neutralized by the addition of a saturated aqueous ammonium chloride solution. The solvents are evaporated under reduced pressure and water and dichloromethane are added. The organic phase is washed 5 times with water and then dried over magnesium sulfate. Ethyl trans-(4-{4-[benzyl(tert-butoxycarbonyl)amino]cyclohexyl}phenoxy)acetate is obtained in the form of a white solid (4.68 g, 100%) after evaporation of the solvents under reduced pressure.

2.2: Ethyl trans-{4-[4-(benzylamino)cyclohexyl]phenoxy}acetate

A solution of 4.5 g of ethyl trans-(4-{4-[benzyl(tert-butoxycarbonyl)amino]cyclohexyl}-phenoxy)acetate (9.6 mmol) in a mixture of trifluoroacetic acid (30 ml) and dichloromethane (90 ml) is stirred for 2 h. The solvents are evaporated under reduced pressure and then water, ethyl acetate and a saturated aqueous sodium carbonate solution are added. The organic phase is washed once with water and dried over sodium sulfate. Ethyl trans-{4-[4-(benzylamino)cyclohexyl]phenoxy}acetate is obtained in the form of an oil (3.22 g, 88%) after evaporation of the solvents under reduced pressure. [M+H$^+$]=368.3

2.3: Ethyl trans-(4-{4-[Benzyl((2S)-3-{4-(benzyloxy)-3-[(methylsulfonyl)amino]phenoxy}-2-hydroxypropyl)amino]cyclohexyl}phenoxy)acetate A mixture of 3.22 g of ethyl trans-{4-[4-(benzylamino)cyclohexyl]phenoxy}acetate (8.7 mmol) and 5 g of 4-benzyloxy-3-(N-(tert-butoxycarbonyl)-N-(methylsulfonyl)amino)-1-((2S)-2,3-epoxypropoxy)benzene (11.2 mmol) in ethanol (72 ml) is brought to reflux for 40 h. A 3N solution of hydrochloric acid in ethanol is added and the reaction medium is heated at 50° C. for 19 h. The solvents are evaporated under reduced pressure and then water, dichloromethane and a saturated aqueous sodium carbonate solution are added. The aqueous phase is extracted once with dichloromethane. The organic phases are combined, washed with water and then dried over magnesium sulfate. The solvents are evaporated under reduced pressure and ethyl trans-(4-{4-[Benzyl((2S)-3-{4-(benzyloxy)-3-[(methylsulfonyl)amino]phenoxy}-2-hydroxypropyl)amino]cyclohexyl}phenoxy)acetate is obtained in the form of an oil (2.7 g, 43%) after purification on silica gel (eluent: ethyl acetate/heptane 30/70 to 50/50 gradient in 40 min). [M+H$^+$]= 717.6

Preparation 3: trans-4-[4-(Benzyl{(2S)-3-[4-(benzyloxy)-3-[(methylsulfonyl)amino]phenoxy]-2-hydroxypropyl}amino)cyclohexyl]benzoic acid (Intermediate product of formula (XII) where $R_1$=Pg=benzyl and $R_2$=—NH—$SO_2$—$CH_3$)

3.1: Ethyl trans-4-[4-(benzylamino)cyclohexyl]benzoate

A solution of 8.51 ml of benzylamine (77.95 mmol) and of 16 g of ethyl 4-(cyclohexanone)benzoate (64.96 mmol) in trimethyl orthoformate (192 ml) is heated at 50° C. for 18 h. The solvents are evaporated under reduced pressure and 267 ml of ethanol are added. 2.457 g of sodium borohydride are subsequently added. The reaction mixture is left stirring for 2 h. The solvents are evaporated under reduced pressure and dichloromethane and water are added. The aqueous phase is extracted three times with dichloromethane. The organic phases are dried over magnesium sulfate and concentrated under reduced pressure. Ethyl trans-4-[4-(benzylamino)cyclohexyl]benzoate is obtained in the form of an oil (14.69 g, 67%) after purification on silica gel (eluent: ethyl acetate/ethanol 90/10). [M+H$^+$]=282.2

3.2: Ethyl trans-4-[4-(benzyl{(2S)-3-[4-(benzyloxy)-3-[(methylsulfonyl)amino]phenoxy]-2-hydroxypropyl}amino)cyclohexyl]benzoate A mixture of 818 mg (1.82 mmol) of 4-benzyloxy-3-(N-(tert-butoxycarbonyl)-N-(methylsulfonyl)amino)-1-((2S)-2,3-epoxypropoxy)benzene and of 450 mg (1.82 mmol) of ethyl trans-4-[4-(benzylamino)cyclohexyl]benzoate in the base form is heated at reflux in 15 ml of absolute ethanol for 16 h. The mixture is cooled, 3 ml of a saturated ethanolic hydrochloric acid solution are added thereto and the mixture is heated at 50° C. for 6 h. The solvent is evaporated and the residue is taken up with a mixture of 50 ml of a saturated sodium bicarbonate solution and 50 ml of ethyl acetate. The organic phase is washed with a saturated aqueous NaCl solution. The organic phase is dried and filtered, and the solvent is evaporated under reduced pressure. The crude product is purified by chromatography on a column of silica gel, elution being carried out with a methylene chloride/methanol/NH$_4$OH (95/5/0.5) mixture. The title compound is obtained in the form of a white solid. [M+H$^+$]=687.

3.3: trans-4-[4-(Benzyl{(2S)-3-[4-(benzyloxy)-3-[(methylsulfonyl)amino]phenoxy]-2-hydroxypropyl}amino)cyclohexyl]benzoic acid A mixture of 4.48 g (5.71 mmol) of ethyl trans-4-[4-(benzyl{(2S)-3-[4-(benzyloxy)-3-[(methylsulfonyl)amino]phenoxy]-2-hydroxypropyl}amino)cyclohexyl]benzoate and of 38 ml of a 1N aqueous sodium hydroxide solution in 114 ml of ethanol is heated overnight at 50° C. The solvents are evaporated, the residue is taken up in water and a 1N hydrochloric acid solution is gently added to pH=1. The precipitate is filtered off and dried under vacuum. The title compound is thus obtained in the form of a white solid (4.05 g, 94%) Melting point=160° C.

Preparation 4: trans-4-[4-(Benzyl{(2S)-3-[4-(benzyloxy)-3-(methylsulfonyl)phenoxy]-2-hydroxypropyl}amino)cyclohexyl]benzoic acid (Intermediate product of formula (XII) where $R_1$=Pg=benzyl and $R_2$=—$SO_2$—$CH_3$)

4.1: Ethyl trans-4-[4-(benzyl{(2S)-3-[4-(benzyloxy)-3-(methylsulfonyl)phenoxy]-2-hydroxypropyl}amino)cyclohexyl]benzoate This product is obtained by carrying out the preparation as described in preparation 3.2 above, using ethyl trans-4-[4-(benzylamino)cyclohexyl]benzoate and 4-benzyloxy-3-methylsulfonyl-1-((2S)-2,3-epoxypropoxy)benzene, disclosed in patent application WO 99/65895, and without adding thereto the solution of hydrochloric acid in ethanol. [M+H$^+$]=672

4.2: trans-4-[4-(Benzyl{(2S)-3-[4-(benzyloxy)-3-(methylsulfonyl)phenoxy]-2-hydroxypropyl}amino)cyclohexyl]benzoic acid The preparation is carried out in a similar way to preparation 3.3 above but using ethyl trans-4-[4-(benzyl{(2S)-3-[4-(benzyloxy)-3-(methylsulfonyl)phenoxy]-2-hydroxypropyl}amino)cyclohexyl]benzoate. 8.13 g (95%) of the title compound are thus obtained in the form of a white solid (melting point=128-130° C.).

EXAMPLE 1 trans-N-{5-[((2S)-3-{[4-(1,1'-Biphenyl-4-yl)cyclohexyl]amino}-2-hydroxypropyl)oxy]-2-hydroxyphenyl}methanesulfonamide (Compound No. 4)

1.1: trans-N-[5-[((2S)-3-{Benzyl[4-(1,1'-biphenyl-4-yl)cyclohexyl]amino}-2-hydroxypropyl)oxy]-2-(benzyloxy)phenyl]methanesulfonamide A mixture of 0.3 g (0.39 mmol) of trans-4{4-[benzyl((2S)-3-{4-(benzyloxy)-3-[(methylsulfonyl)amino]phenoxy}-2-hydroxypropyl)amino]cyclohexyl}phenyl trifluoromethanesulfonate (preparation 1), of 0.143 g of phenylboronic acid (1.76 mmol), of 0.091 g of tetrakis(triphenylphosphine)palladium (0.078 mmol) and of 0.198 g of sodium hydrogencarbonate (3.52 mmol) in ethanol (5 ml) and water (2.5 ml) is brought to reflux for 1 hour. Water and dichloromethane are subsequently added and the reaction mixture is filtered. The organic phase is dried over magnesium sulfate. The solvents are evaporated under reduced pressure and trans-N-[5-[((2S)-3-{benzyl[4-(1,1'-biphenyl-4-yl)cyclohexyl]amino}-2-hydroxypropyl)oxy]-2-(benzyloxy)phenyl]methanesulfonamide is obtained in the form of a white solid (0.16 g, 60%) after purification on silica gel (eluent: heptane/ethyl acetate 95/5 to 50/50 gradient in 20 minutes and 50/50 gradient for 15 minutes). [M+H$^+$]=691.5

1.2: trans-N-{5-[((2S)-3-{[4-(1,1'-Biphenyl-4yl)cyclohexyl]amino}-2-hydroxypropyl)oxy]-2-hydroxyphenyl}methanesulfonamide A mixture of 0.16 g of trans-N-[5-[((2S)-3-{benzyl[4-(1,1'-biphenyl-4-yl)cyclohexyl]amino}-2-hydroxypropyl)oxy]-2-(benzyloxy)phenyl]methanesulfonamide (0.23 mmol) and of 0.1 g of 10% palladium-on-charcoal (50% in water) in ethanol (6 ml) is placed under a hydrogen atmosphere and stirred for 4 hours. The reaction mixture is filtered through celite. The solvents are evaporated under reduced pressure and trans-N-{5-[((2S)-3-{[4-(1,1'-biphenyl-4-yl)cyclohexyl]amino}-2-hydroxypropyl)oxy]-2-hydroxyphenyl}methanesulfonamide is obtained in the form of a white solid (0.08 g, 68%) after purification on silica gel (eluent: dichloromethane/methanol, 99/1 to 85/15 gradient in 30 minutes).

Melting point=100-110° C.; [M+H$^+$]=511.4; $^1$H NMR (d$_6$-DMSO+D$_2$O, 200 MHz): 1.05-1.35 (m, 2H), 1.4-1.6 (m, 2H), 1.7-2 (m, 5H), 2.4-2.8 (m, 3H), 2.85 (s, 3H), 3.7-3.85 (m, 3H), 6.52 (dd, 1H), 6.7-6.82 (m, 2H), 7.2-7.65 (m, 9H).

EXAMPLE 2 trans-N-{2-Hydroxy-5-[((2S)-2-hydroxy-3-{[4-(4-hydroxyphenyl)cyclohexyl]amino}propyl)oxy]phenyl}methanesulfonamide (Compound No. 1)

2.1: trans-N-[5-[((2S)-3-{Benzyl[4-(4-hydroxyphenyl)cyclohexyl]amino}-2-hydroxypropyl)oxy]-2-(benzyloxy)phenyl]methanesulfonamide A mixture of 1.52 g (3.38 mmol) of 4-benzyloxy-3-(N-(tert-butoxycarbonyl)-N-(methylsulfonyl)amino)-1-((2S)-2,3-epoxypropoxy)benzene and of 1 g (3.55 mmol) of trans-4-[4-(benzylamino)cyclohexyl]phenol in the base form is heated at reflux in 20 ml of absolute ethanol for 16 h. The mixture is cooled, 20 ml of a saturated ethanolic hydrochloric acid solution are added thereto and the mixture is heated at 50° C. for 1 h. The solvent is evaporated and the residue is taken up in a mixture of 100 ml of a saturated sodium bicarbonate solution and 100 ml of ethyl acetate. The organic phase is washed with a saturated aqueous NaCl solution. The organic phase is dried and filtered, and the solvent is evaporated under reduced pressure. The crude product is purified by chromatography on a column of silica gel, elution being carried out with a heptane/ethyl acetate (55/45) mixture. The title compound is obtained in the form of a white solid (1.8 g, 84%). [M+H$^+$]=631.5

2.2: trans-N-{2-Hydroxy-5-[((2S)-2-hydroxy-3-{[4-(4-hydroxyphenyl)cyclohexyl]amino}propyl)oxy]phenyl}methanesulfonamide A mixture of 0.8 g (1.26 mmol) of trans-N-[5-[((2S)-3-{benzyl[4-(4-hydroxyphenyl)cyclohexyl]amino}-2-hydroxypropyl)oxy]-2-(benzyloxy)phenyl]methanesulfonamide and of 0.2 g of 10% palladium-on-charcoal (50% in water) in ethanol (40 ml) is placed under hydrogen atmosphere and stirred for 2 h. The reaction mixture is filtered through celite. The solvents are evaporated under reduced pressure and trans-N-{2-hydroxy-5-[((2S)-2-hydroxy-3-{[4-(4-hydroxyphenyl)cyclohexyl]amino}propyl)oxy]phenyl}methanesulfonamide is obtained in the form of a white solid (0.24 g, 67%) after purification on silica gel (eluent: dichloromethane/methanol, 95/5 to 80/20 gradient in 15 min).

Melting point=85-90° C.; [M+H$^+$]=451.4; $^1$H NMR (d$_6$-DMSO, 300 MHz): 1.15 (dd, 2H), 1.38 (dd, 2H), 1.68-1.8 (m, 2H), 1.85-2 (m, 2H), 2.25-2.52 (m, 3H), 2.61 (dd, 1H), 2.75 (dd, 1H), 2.91 (s, 3H), 3.7-3.9 (m, 3H), 6.55 (dd, 1H), 6.65 (d, 2H), 6.75-6.8 (m, 2H), 6.95 (d, 2H).

EXAMPLE 3

Ethyl trans-(4-{4-[((2S)-2-hydroxy-3-{4-hydroxy-3-[(methylsulfonyl)amino]phenoxy}propyl)amino]cyclohexyl}phenoxy)acetate (Compound No. 2)

A mixture of ethyl trans-(4-{4-[benzyl((2S)-3-{4-(benzyloxy)-3-[(methylsulfonyl)amino]phenoxy}-2-hydroxypropyl)amino]cyclohexyl}phenoxy)acetate (0.26 mmol) and of 0.25 g of 10% palladium-on-charcoal (50% in water) in ethanol (16 ml) is placed under hydrogen atmosphere and stirred for 7 h. The reaction mixture is filtered through celite. The solvents are evaporated under reduced pressure and ethyl trans-(4-{4-[((2S)-2-hydroxy-3-{4-hydroxy-3-[(methylsulfonyl)amino]phenoxy}propyl)amino]cyclohexyl}-phenoxy)acetate is obtained in the form of a white solid (0.08 g, 54%) after purification on silica gel (eluent: dichloromethane/methanol, 99/1 to 85/15 gradient in 30 min).

Melting point=60-70° C.; [M+H$^+$]=537.6; $^1$H NMR (d$_6$-DMSO+D$_2$O, 200 MHz): 1.1-1.5 (m, 4H), 1.2 (t, 3H), 1.65-1.8 (m, 2H), 1.85-2 (m, 2H), 2.3-2.85 (m, 4H), 2.93 (s, 3H), 3.7-3.9 (m, 3H), 4.18 (q, 2H), 4.7 (s, 2H), 6.55 (dd, 1H), 6.7-6.85 (m, 4H), 7.08 (d, 2H)

EXAMPLE 4 trans-(4-{4-[((2S)-2-Hydroxy-3-{4-hydroxy-3-[(methylsulfonyl)amino]phenoxy}propyl)amino]cyclohexyl}phenoxy)acetic acid (Compound No. 3)

4.1: trans-(4-{4-[Benzyl((2S)-3-{4-(benzyloxy)-3-[(methylsulfonyl)amino]phenoxy}-2-hydroxypropyl)amino]cyclohexyl}phenoxy)acetic acid A mixture of 0.36 g of ethyl trans-(4-{4-[benzyl((2S)-3-{4-(benzyloxy)-3-[(methylsulfonyl)amino]phenoxy}-2-hydroxypropyl)amino]cyclohexyl}phenoxy)acetate (0.49 mmol) and of 6 ml of a molar aqueous sodium hydroxide solution in ethanol (10 ml) is heated at 45° C. for 22 h. The solvents are subsequently evaporated under reduced pressure and water is added. A molar aqueous hydrochloric acid solution is subsequently added to pH=1. The title product is obtained in the form of a white solid (0.3 g, 89%) after filtration and drying under vacuum. {M+H$^+$]=689.7

4.2: trans-(4-{4-[((2S)-2-Hydroxy-3-{4-hydroxy-3-[(methylsulfonyl)amino]phenoxy}propyl)amino]cyclohexyl}phenoxy)acetic acid A mixture of 0.3 g of trans-(4-{4-[benzyl((2S)-3-{4-(benzyloxy)-3-[(methylsulfonyl)amino]phenoxy}-2-hydroxypropyl)amino]cyclohexyl}phenoxy)acetic acid (0.44 mmol) and of 0.20 g of 10% palladium-on-charcoal (50% in water) in a mixture of tetrahydrofuran (5 ml) and ethanol (5 ml) is placed under a hydrogen atmosphere and stirred for 4 h. The reaction mixture is filtered through celite. The solvents are evaporated under reduced pressure and trans-(4-{4-[((2S)-2-hydroxy-3-{4-hydroxy-3-[(methylsulfonyl)amino]phenoxy}propyl)amino]cyclohexyl}-phenoxy)acetic acid is obtained in the form of a white solid (0.07 g, 32%) after purification on C$_{18}$-grafted silica (eluent: water/acetonitrile, 95/5 to 5/95 gradient in 15 min).

Melting point=160-170° C.; [M+H$^+$]=509.6; $^1$H NMR (d$_6$-DMSO+D$_2$O, 200 MHz): 1.1-1.45 (m, 4H), 1.6-2 (m, 4H), 2.1-2.25 (m, 1H), 2.6-3.1 (m, 4H), 2.95 (s, 3H), 3.75-3.9 (m, 2H), 4-4.15 (m, 1H), 4.28 (s, 2H), 6.55-6.82 (m, 5H), 7.05 (d, 2H).

EXAMPLE 5

Ethyl trans-N-(4-{4-[((2S)-2-hydroxy-3-{4-hydroxy-3-[(methylsulfonyl)amino]phenoxy}propyl)amino]cyclohexyl}benzoyl)-L-valinate (Compound No. 13)

5.1: Ethyl trans-(2S)-2-[(4-{4-[benzyl((2S)-3-{4-(benzyloxy)-3-[(methylsulfonyl)amino]phenoxy}-2-hydroxypropyl)amino]cyclohexyl}benzoyl)amino]-3-methylbutanoate A solution of 0.3 g (0.45 mmol) of trans-4-[4-(benzyl{(2S)-3-[4-(benzyloxy)-3-[(methylsulfonyl)amino]phenoxy]-2-hydroxypropyl}amino)cyclohexylbenzoic acid (preparation 3), of 0.78 g (0.91 mmol) of 1-hydroxybenzotriazole, of 0.175 g (0.91 mmol) of 1-ethyl-3-(3-dimethylaminopropyl)carbodiimide hydrochloride, of 0.19 ml of triethylamine and of 0.165 g (0.91 mmol) of L-valine ethyl ester hydrochloride in 5 ml of dichloromethane is stirred for 24 h. The solvents are evaporated under reduced pressure. Dichloromethane and water are added and the organic phase is washed three times with water. The organic phases are dried over magnesium sulfate and concentrated under reduced pressure. Ethyl trans-(2S)-2-[(4-{4-[benzyl((2S)-3-{4-(benzyloxy)-3-[(methylsulfonyl)amino]phenoxy}-2-hydroxypropyl)amino]-cyclohexyl}benzoyl)amino]-3-methylbutanoate is obtained in the form of a yellow oil (0.35 g, 98%). {M+H$^+$}=786

5.2: Ethyl trans-N-(4-{4-[((2S)-2-hydroxy-3-{4-hydroxy-3-[(methylsulfonyl)amino]phenoxy}propyl)amino]cyclohexyl}benzoyl)-L-valinate A suspension of 1.35 g (0.35 mmol) of ethyl trans-(2S)-2-[(4-{4-[benzyl((2S)-3-{4-(benzyloxy)-3-[(methylsulfonyl)amino]phenoxy}-2-hydroxypropyl)amino]cyclohexyl}benzoyl)amino]-3-methylbutanoate and of 0.177 g of palladium-on-charcoal (10% Pd, 50% in water) in 15 ml of ethanol is placed under hydrogen atmosphere and stirred for 3 h. The catalyst is subsequently filtered off and the solvents are evaporated under reduced pressure. The title compound is obtained in the form of a white solid (0.138 g, 44%) after purification on silica gel (eluent: dichloromethane/methanol/aqueous ammonia 99/1/0.1 to 85/15/1.5 gradient in 30 min).

Melting point=65-75° C.; $^1$H NMR (d$_6$-DMSO+D$_2$O, 200 MHz): 0.92 (t, 3H), 1.1-1.35 (m, 8H), 1.35-1.6 (m, 2H), 1.7-2.25 (m, 5H), 2.4-2.8 (m, 4H), 2.92 (s, 3H), 3.6-3.9 (m, 3H), 4-4.2 (m, 2H), 4.25 (t, 1H), 6.6 (dd, 1H), 6.68-6.8 (m, 2H), 7.32 (d, 2H), 7.78 (d, 2H).

EXAMPLE 6 trans-N-(4-{4-[((2S)-2-Hydroxy-3-{4-hydroxy-3-[(methylsulfonyl)amino]phenoxy}propyl)amino]cyclohexyl}benzoyl)-L-phenylalanine (Compound No. 19)

6.1: Ethyl trans-N-(4-{4-[benzyl((2S)-3-{4-(benzyloxy)-3-[(methylsulfonyl)amino]phenoxy}-2-hydroxypropyl)amino]cyclohexyl}benzoyl)-L-phenylalaninate A solution of 0.3 g (0.45 mmol) of trans-4-[4-(benzyl{(2S)-3-[4-(benzyloxy)-3-[(methylsulfonyl)amino]phenoxy]-2-hydroxypropyl}amino)cyclohexyl]benzoic acid (preparation 3), of 0.78 g (0.91 mmol) of 1-hydroxybenzotriazole, of 0.175 g (0.91 mmol) of 1-ethyl-3-(3-dimethylaminopropyl)carbodiimide hydrochloride, of 0.19 ml of triethylamine and of 0.165 g (0.91 mmol) of L-phenylalanine ethyl ester hydrochloride in 5 ml of dichloromethane is stirred for 24 h. The solvents are evaporated under reduced pressure. Dichloromethane and water are added and the organic phase is washed three times with water. The organic phases are dried over magnesium sulfate and concentrated under reduced pressure. The product is obtained in the form of a white solid (0.350 g, 92%) after purification on silica gel (eluent: dichloromethane/methanol 100/00 to 90/10 gradient in 35 min). [M+H$^+$]=835

6.2: trans-N-(4-{4-[Benzyl((2S)-3-{4-(benzyloxy)-3-[(methylsulfonyl)amino]phenoxy}-2-hydroxypropyl)amino]cyclohexyl}benzoyl)-L-phenylalanine A mixture of 0.35 g of ethyl trans-N-(4-{4-[benzyl((2S)-3-{4-(benzyloxy)-3-[(methylsulfonyl)amino]phenoxy}-2-hydroxypropyl)-amino]cyclohexyl}benzoyl)-L-phenylalaninate (0.42 mmol) and of 1.7 ml of a molar aqueous sodium hydroxide solution in ethanol (9.3 ml) is heated at 45° C. for 3 h. The solvents are subsequently evaporated under reduced pressure and water is added. A molar aqueous hydrochloric acid solution is subsequently added to pH=1. The title product is obtained in the form of a white solid (0.2 g, 59%) after filtration and drying under vacuum [M+H$^+$]=807.

6.3: trans-N-(4-{4-[((2S)-2-Hydroxy-3-{4-hydroxy-3-[(methylsulfonyl)amino]phenoxy}propyl)amino]cyclohexyl}benzoyl)-L-phenylalanine A mixture of 0.2 g of trans-N-(4-{4-[benzyl((2S)-3-{4-(benzyloxy)-3-[(methylsulfonyl)-amino]phenoxy}-2-hydroxypropyl)amino]cyclohexyl}-benzoyl)-L-phenylalanine (0.248 mmol) and of 0.1 g of 10% palladium-on-charcoal (50% in water) in ethanol (15 ml) is placed under hydrogen atmosphere and stirred for 3 h. The reaction mixture is filtered through celite. The solvents are evaporated under reduced pressure and trans-N-(4-{4-[((2S)-2-hydroxy-3-{4-hydroxy-3-[(methylsulfonyl)amino]phenoxy}propyl)amino]cyclohexyl}benzoyl)-L-phenylalanine is obtained in the form of a white solid (0.049 g, 31%) after purification on C$_{18}$-grafted silica (eluent: water/acetonitrile, 95/5 to 5/95 gradient in 15 min).

Melting point >230° C.; [M+H$^+$]=626.4; $^1$H NMR (d$_6$-DMSO+D$_2$O, 200 MHz): 1.1-1.65 (m, 6H), 1.9-2.1 (m, 2H), 2.2-2.38 (m, 1H), 2.7-3.3 (m, 4H), 2.92 (s, 3H), 3.75-3.9 (m, 3H), 4-4.2 (m, 1H), 4.25-4.4 (m, 1H), 6.65 (dd, 1H), 6.75-6.9 (m, 2H), 7-7.3 (m, 7H), 7.68 (d, 2H).

EXAMPLE 7 trans-4-[4-({(2S)-2-Hydroxy-3-[4-hydroxy-3-(methylsulfonyl)phenoxy]propyl}amino)cyclohexyl]-N'-phenylbenzohydrazide (Compound No. 26)

7.1: trans-4-[4-(Benzyl{(2S)-3-[4-(benzyloxy)-3-(methylsulfonyl)phenoxy]-2-hydroxypropyl}amino)cyclohexyl]-N'-phenylbenzohydrazide A solution of 0.3 g (0.441 mmol) of trans-4-[4-(benzyl{(2S)-3-[4-(benzyloxy)-3-(methylsulfonyl)phenoxy]-2-hydroxypropyl}amino)cyclohexyl]benzoic acid (preparation 4), of 0.78 g (0.91 mmol) of 1-hydroxybenzotriazole, of 0.169 g (0.88 mmol) of 1-ethyl-3-(3-dimethylaminopropyl)carbodiimide hydrochloride, of 0.184 ml of triethylamine and of 0.095 g (0.88 mmol) of phenylhydrazine in a mixture of 4 ml of dichloromethane and 0.8 ml of acetonitrile is stirred for 48 hours. The solvents are evaporated under reduced pressure. Dichloromethane and water are added and the organic phase is washed three times with water. The organic phases are dried over magnesium sulfate and concentrated under reduced pressure. The product is obtained in the form of a white solid (0.166 g, 50%) after purification on silica gel (eluent: heptane/ethyl acetate 60/40 for 10 min, 60/40 to 40/60 in 10 min, then 40/60 for 20 min gradient). [M+H$^+$]=734.7

7.2: trans-4-[4-({(2S)-2-Hydroxy-3-[4-hydroxy-3-(methylsulfonyl)phenoxy]propyl}amino)cyclohexyl]-N'-phenylbenzohydrazide A mixture or 0.166 g of trans-4-[4-(benzyl{(2S)-3-[4-(benzyloxy)-3-(methylsulfonyl)phenoxy]-2-hydroxypropyl}amino)cyclohexyl]-N'-phenylbenzohydrazide (0.226 mmol) and of 0.1 g of 10% palladium-on-charcoal (50% in water) in a mixture of ethanol (3.9 ml) and tetrahydrofuran (2.93 ml) is placed under hydrogen atmosphere and stirred for 48 h. The catalyst is subsequently filtered off and the solvents are evaporated under reduced pressure. The title compound is obtained in the form of a white solid (0.02 g, 16%) after purification on silica gel (eluent: dichloromethane/methanol/aqueous ammonia 99/1/0.1 to 85/15/1.5 gradient in 30 min).

Melting point=125° C.; [M+H$^+$]=554; $^1$H NMR (d$_6$-DMSO, 200 MHz): 1.0-1.6 (m, 4H), 1.7-2.1 (m, 4H), 2.35-2.8 (m, 4H), 2.7-3.3 (m, 4H), 3.2 (s, 3H), 3.7-3.95 (m, 3H), 4-4.2 (m, 1H), 4.25-4.4 (m, 1H), 6.65 (dd, 1H), 6.6-7.4 (m, 9H), 7.75-7.9 (m, 3H)

EXAMPLE 8 trans-N-(4-Fluorobenzyl)-4-[4-({(2S)-2-hydroxy-3-[4-hydroxy-3-(methylsulfonyl)phenoxy]propyl}amino)cyclohexyl]benzamide (Compound No. 25)

8.1: trans-4-[4-(Benzyl{(2S)-3-[4-(benzyloxy)-3-(methylsulfonyl)phenoxy]-2-hydroxypropyl}amino)cyclohexyl]-N-(4-fluorobenzyl)benzamide A solution of 0.3 g (0.441 mmol) of trans-4-[4-(benzyl{(2S)-3-[4-(benzyloxy)-3-(methylsulfonyl)phenoxy]-2-hydroxypropyl}amino)cyclohexyl]benzoic acid (preparation 4), of 0.78 g (0.91 mmol) of 1-hydroxybenzotriazole, of 0.169 g (0.88 mmol) of 1-ethyl-3-(3-dimethylaminopropyl)carbodiimide hydrochloride, of 0.184 ml of triethylamine and of 0.11 g (0.88 mmol) of 4-fluorobenzylamine in a mixture of 4 ml of dichloromethane and 0.8 ml of acetonitrile is stirred for 48 h. The solvents are evaporated under reduced pressure. Dichloromethane and water are added and the organic phase is washed three times with water. The organic phases are dried over magnesium sulfate and concentrated under reduced pressure. The product is obtained in the form of a white solid (0.232 g, 70%) after purification on silica gel (eluent: heptane/ethyl acetate 60/40 for 10 min, 60/40 to 40/60 in 10 min and then 40/60 for 20 min gradient). [M+H$^+$]=751.5

8.2: trans-N-(4-Fluorobenzyl)-4-[4-({(2S)-2-hydroxy-3-[4-hydroxy-3-(methylsulfonyl)phenoxy]propyl}amino)cyclohexyl]benzamide A mixture of 0.166 g of trans-4-[4-(benzyl{(2S)-3-[4-(benzyloxy)-3-(methylsulfonyl)phenoxy]-2-hydroxypropyl}amino)cyclohexyl]-N-(4-fluorobenzyl)benzamide (0.226 mmol) and of 0.117 g of 10% palladium-on-charcoal (50% in water) in a mixture of ethanol (5.3 ml) and tetrahydrofuran (4.02 ml) is placed under a hydrogen atmosphere and stirred for 48 hours. The catalyst is subsequently filtered off and the solvents are evaporated under reduced pressure. The title compound is obtained in the form of a white solid (0.92 g, 52%) after purification on silica gel (eluent: dichloromethane/methanol/aqueous ammonia 99/1/0.1 to 85/15/1.5 gradient in 30 min).

Melting point 110° C.; [M+H$^+$]=571; $^1$H NMR (d$_6$-DMSO, 500 MHz): 1.12-1.2 (m, 2H), 1.4-1.5 (m, 2H), 1.7-1.8 (m, 2H), 1.9-2 (m, 2H), 2.45-2.55 (m, 2H), 2.6-2.68 (m, 1H), 2.7-2.8 (m, 1H), 3.22 (s, 3H), 3.75-3.95 (m, 3H), 4.4 (s, 2H), 6.88 (dd, 1H), 7.08-7.2 (m, 4H), 7.28-7.3 (m, 3H), 7.74 (d, 2H).

EXAMPLE 9 trans-4-{4-[((2S)-2-Hydroxy-3-{4-hydroxy-3-[(methylsulfonyl)amino]phenoxy}propyl)amino]cyclohexyl}-N-[2-(1H-indol-3-yl)ethyl]benzamide (Compound No. 29)

9.1: trans-4-{4-[Benzyl((2S)-3-{4-(benzyloxy)-3-[(methylsulfonyl)amino]phenoxy}-2-hydroxypropyl)-amino]cyclohexyl}-N-[2-(1H-indol-3-yl)ethyl]benzamide A solution of 0.3 g (0.45 mmol) of trans-4-[4-(benzyl{(2S)-3-[4-(benzyloxy)-3-[(methylsulfonyl)amino]phenoxy]-2-hydroxypropyl}amino)cyclohexyl]benzoic acid (preparation 3), of 0.78 g (0.91 mmol) of 1-hydroxybenzotriazole, of 0.175 g (0.91 mmol) of 1-ethyl-3-(3-dimethylaminopropyl)carbodiimide, of 0.19 ml of triethylamine and of 0.138 g (0.86 mmol) of tryptamine in a mixture of 4 ml of dichloromethane and 0.8 ml of acetonitrile is stirred for 24 h. The solvents are evaporated under reduced pressure. Dichloromethane and water are added and the organic phase is washed three times with water. The organic phases are dried over magnesium sulfate and concentrated under reduced pressure. The title compound is obtained in the form of a white solid (0.246 g, 58%) after purification on silica gel (eluent: heptane/ethyl acetate 60/40 for 10 min, 60/40 to 40/60 in 10 min and then 40/60 for 20 min gradient). [M+H$^+$]=801.6

9.2: trans-4-{4-[((2S)-2-Hydroxy-3-{4-hydroxy-3-[(methylsulfonyl)amino]phenoxy}propyl)amino]cyclohexyl}-N-[2-(1H-indol-3-yl)ethyl]benzamide A suspension of 0.246 g (0.3 mmol) of trans-4-{4-[benzyl((2S)-3-{4-(benzyloxy)-3-[(methylsulfonyl)amino]phenoxy}-2-hydroxypropyl)amino]cyclohexyl}-N-[2-(1H-indol-3-yl)ethyl]benzamide and of 0.332 g of palladium-on-charcoal (10% Pd, 50% in water) in a mixture of 5.4 ml of ethanol and 4 ml of tetrahydrofuran is placed under hydrogen atmosphere and is stirred for 3 h. The catalyst is subsequently filtered off and the solvents are evaporated under reduced pressure. The title compound is obtained in the form of a white solid (0.076 g, 40%) after purification on silica gel (eluent: dichloromethane/methanol/aqueous ammonia 99/1/0.1 to 85/15/1.5 gradient in 30 min).

Melting point=125° C.; [M+H$^+$]=621; $^1$H NMR (d$_6$-DMSO, 200 MHz): 1-1.2 (m, 2H), 1.3-1.55 (m, 2H), 1.7-2 (m, 4H), 2.4-3 (m, 6H), 2.9 (s, 3H), 3.4-3.6 (m, 2H), 3.7-3.8 (m, 1H), 3.8-3.95 (m, 3H), 6.6 (dd, 1H), 6.7-6.85 (m, 2H), 6.9-7.2 (m, 3H), 7.25-7.4 (m, 3H), 7.55 (d, 1H), 7.75 (d, 2H), 8.4-8.5 (m, 1H).

EXAMPLE 10

Ethyl trans-2-{4-[4-({(2S)-3-[3-(butylsulfinyl)-4-hydroxyphenoxy]-2-hydroxypropyl}amino)cyclohexyl]phenoxy}-2,2-dimethylacetate (Compound No. 34)

10.1: Ethyl trans-2-[4-(4-aminocyclohexyl)phenoxy]-2,2-dimethylacetate hydrochloride A mixture of 1.9 g of ethyl trans-2-{4-[4-(benzylamino)cyclohexyl]phenoxy}-2,2-dimethylacetate in the base form (4.8 mmol) and of 0.1 g of 10% palladium-on-charcoal in ethanol (75 ml) is placed under hydrogen atmosphere at 40° C. and stirred for 7 h. The reaction mixture is filtered through celite. The solvent is evaporated under reduced pressure and ethyl trans-2-[4-(4-aminocyclohexyl)phenoxy]-2,2-dimethylacetate is obtained (0.660 g) in the form of a yellow oil which is dissolved in ethanol (5 ml). The solution is acidified with a solution (9N) of HCl in ethanol and the solid thus obtained is filtered off (0.530 g, 72%). Melting point: 240-242.

10.2: Ethyl trans-2-{4-[4-({(2S)-3-[4-(benzyloxy)-3-(butylsulfinyl)phenoxy]-2-hydroxypropyl}amino)-cyclohexyl]phenoxy}-2,2-dimethylacetate A mixture of 0.742 g of (2S)-2-{[4-(benzyloxy)-3-(butylsulfinyl)phenoxy]methyl}oxirane (obtained by analogy with the method disclosed in WO 99/65895 but starting from the butyl sulfoxide instead of the methyl sulfoxide and using (S)-(+)-glycidyl nosylate; $[\alpha]_D$=+1.9 (c=1%, MeOH)) (2.06 mmol) and of 0.666 g of ethyl trans-2-[4-(4-aminocyclohexyl)phenoxy]-2,2-dimethylacetate hydrochloride (2.18 mmol) in ethanol (25 ml) is heated to reflux overnight. The solvent is evaporated under reduced pressure and the product obtained is purified by flash chromatography, elution being carried out with a methylene chloride/methanol/aqueous ammonia (95/5/0.5) mixture. The title product is obtained in the form of a yellow oil (0.730 g, 53%).

10.3: Ethyl trans-2-{4-[4-({(2S)-3-[3-(butylsulfinyl)-4-hydroxyphenoxy]-2-hydroxypropyl}amino)cyclohexyl]phenoxy}-2,2-dimethylacetate A solution of 0.720 g of ethyl trans-2-{4-[4-({(2S)-3-[4-(benzyloxy)-3-(butylsulfinyl)phenoxy]-2-hydroxypropyl}amino)cyclohexyl]phenoxy}-2,2-dimethylacetate (1.08 mmol) in trifluoroacetic acid (12 ml) is heated at 60° C. for 3 hours. The solvent is evaporated and the residue is treated with a sodium bicarbonate solution and ethyl acetate. The organic phase is separated, dried, filtered and evaporated under vacuum. The product thus obtained is purified by flash chromatography, elution being carried out with a methylene chloride/methanol/aqueous ammonia (9/1/0.1) mixture. The title product is obtained in the form of a solid (0.31 g, 50%).

Melting point=58-60° C.; $[M+H^+]$=576; $^1$H NMR ($d_6$-DMSO, 313K): 0.86 (t, 3H, J=7 Hz), 1.17 (t, 3H, J=7 Hz), 1.05-1.24 (m, 2H), 1.27-1.46 (m, 2H), 1.49 (s, 6H), 1.60-1.72 (m, 1H), 1.77 (bd, 2H, J=13 Hz), 1.96 (bd, 2H, J=13 Hz), 2.30-2.47 (m, 2H), 2.58-2.83 (m, 3H), 2.93-3.09 (m, 1H), 3.74-3.89 (m, 2H), 3.89-3.98 (m, 1H), 4.16 (q, 2H, J=7 Hz), 6.71 (m, 2H), 6.81 (d, 1H, J=9 Hz), 6.92 (dd, 1H, Ja=9 Hz, Jb=3 Hz); 7.07 (d, 1H, J=3 Hz); 7.10 (m, 2H).

The chemical structures and the physical properties of a few compounds according to the invention are illustrated in the following table. In this table:

- in the "salt" column, "-" represents a compound in the free base form,
- Me, Et, iPr, nBu, iBu, Ph and Bn respectively represent the methyl, ethyl, isopropyl, butyl, isobutyl, phenyl and benzyl groups.

TABLE (I)

| No. | $R_1$ | $R_2$ | $R_3$ | Salt | Melting point (° C.) |
|---|---|---|---|---|---|
| 1 | H | —NHSO$_2$CH$_3$ | —OH | — | 85-90 |
| 2 | H | —NHSO$_2$CH$_3$ | —O—CH$_2$—COOEt | — | 60-70 |
| 3 | H | —NHSO$_2$CH$_3$ | —O—CH$_2$—COOH | — | 160-170 |
| 4 | H | —NHSO$_2$CH$_3$ | —C$_6$H$_5$ | — | 100-110 |

TABLE-continued
(I)
| No. | R₁ | R₂ | R₃ | Salt | Melting point (°C.) |
|---|---|---|---|---|---|
| 5 | H | —NHSO$_2$CH$_3$ | 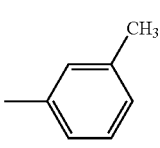 | — | 90-95 |
| 6 | H | —NHSO$_2$CH$_3$ | 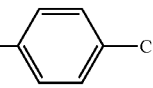 | — | 95-100 |
| 7 | H | —NHSO$_2$CH$_3$ | 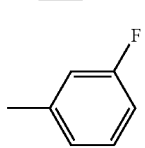 | — | 140-150 |
| 8 | H | —NHSO$_2$CH$_3$ | 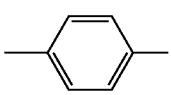 | — | 105-110 |
| 9 | H | —NHSO$_2$CH$_3$ | 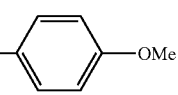 | — | 120-125 |
| 10 | H | —NHSO$_2$CH$_3$ | 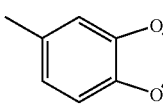 | — | 165-175 |
| 11 | H | —NHSO$_2$CH$_3$ | 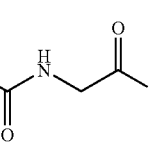 | — | 215-220 |
| 12 | H | —NHSO$_2$CH$_3$ | 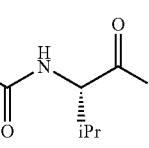 | — | 64-69 |
| 13 | H | —NHSO$_2$CH$_3$ | 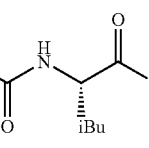 | — | 65-75 |
| 14 | H | —NHSO$_2$CH$_3$ |  | — | 65-80 |

TABLE-continued (I)

[Structure: R₁O-(phenyl with R₂)-O-CH₂-CH(OH)-CH₂-NH-(cyclohexyl)-(phenyl with R₃)]

| No. | R₁ | R₂ | R₃ | Salt | Melting point (°C.) |
|---|---|---|---|---|---|
| 15 | H | —NHSO₂CH₃ | N-acetyl-Phe-OEt | — | 73-83 |
| 16 | H | —NHSO₂CH₃ | N-acetyl-Tyr-OEt | — | 70-80 |
| 17 | H | —NHSO₂CH₃ | N-acetyl-Val-OH (iPr) | — | 150-180 |
| 18 | H | —NHSO₂CH₃ | N-acetyl-Leu-OH (iBu) | — | >250 |
| 19 | H | —NHSO₂CH₃ | N-acetyl-Phe-OH | — | >230 |
| 20 | H | —NHSO₂CH₃ | N-acetyl-Tyr-OH | — | 170-210 |
| 21 | H | —NHSO₂CH₃ | N-acetyl-β-Ala-COOEt | pamoate | 110-150 |

TABLE-continued (I)

Structure: Aryl ether with R₁O- and R₂ substituents on phenyl, connected via -O-CH₂-CH(OH)-CH₂-NH- to a trans-cyclohexyl bearing a 4-R₃-phenyl group.

| No. | R₁ | R₂ | R₃ | Salt | Melting point (°C.) |
|-----|----|----|----|------|---------------------|
| 22 | H | —NHSO₂CH₃ | -NHC(O)CH(COOEt)-CH₂CH₂-COOEt (acetamido diester) | — | 55-65 |
| 23 | H | —NHSO₂CH₃ | -NHC(O)CH(COOH)-CH₂CH₂-COOH (acetamido diacid) | — | 160-200 |
| 24 | H | —NHSO₂CH₃ | -C(O)NH-CH₂-(4-F-C₆H₄) | — | 75-85 |
| 25 | H | —SO₂CH₃ | -C(O)NH-CH₂-(4-F-C₆H₄) | — | 110 |
| 26 | H | —SO₂CH₃ | -C(O)NH-NH-C₆H₅ | — | 125 |
| 27 | H | —SO₂CH₃ | -C(O)NH-NH-(4-F-C₆H₄) | — | 125 |
| 28 | H | —SO₂CH₃ | -C(O)NH-CH₂CH₂-(1H-indol-3-yl) | — | 115 |
| 29 | H | —NHSO₂CH₃ | -C(O)NH-CH₂CH₂-(1H-indol-3-yl) | — | 125 |
| 30 | H | —SO₂CH₃ | -C(O)NH-(9H-fluoren-9-yl) | — | 141 |

TABLE-continued (I)

Structure: R$_1$O-phenyl(R$_2$)-O-CH$_2$-CH(OH)-CH$_2$-NH-cyclohexyl-phenyl-R$_3$

| No. | R$_1$ | R$_2$ | R$_3$ | Salt | Melting point (° C.) |
|---|---|---|---|---|---|
| 31 | H | —SO$_2$CH$_3$ | —C(=O)N(CH$_2$CH$_2$OCH$_3$)$_2$ (acetyl) | — | 80 |
| 32 | H | —NHSO$_2$CH$_3$ | —OC(CH$_3$)$_2$COOEt | — | 45-48 |
| 33 | H | —NHSO$_2$Ph | —OC(CH$_3$)$_2$COOEt | — | 72-74 |
| 34 | H | —SO(nBu) | —OC(CH$_3$)$_2$COOEt | — | 58-60 |
| 35 | H | —SO(nBu) | AcNH-CH(iPr)-COOEt | — | 76-78 |

The compounds according to the invention have formed the subject of pharmacological tests which make it possible to determine their agonist activity effect with regard to β$_3$ receptors.

The agonist activity with regard to β$_3$ receptors (reflected by production of cAMP induced by the test compound) was studied using membrane preparations from SKNMC cells (human neuroblastoma cells) in the presence of selective β$_1$ and β$_2$ antagonists (CGP20712 and ICI118551, both at a concentration of 10$^{-6}$M). The activity of the compounds according to the invention (pKa) is greater than or equal to 6.0 (it is generally between 6.0 and 7.6). Their effectiveness is greater than or equal to 60% and is generally within the range from 60 to 90%.

The activities of the compounds according to the invention toward β$_1$ and β$_2$ receptors were studied on the auricle and on the trachea, respectively, of guinea-pigs. The agonist and antagonist activities were measured. It was thus found that the compounds according to the invention are selective toward β$_3$ receptors: specifically, they are at least 50 times more active toward β$_3$ receptors than toward β$_1$ or β$_2$ receptors.

The compounds according to the invention can thus be used for the preparation of medicaments intended in particular for the treatment of diseases in which β$_3$ receptors are implicated. More particularly, the compounds according to the invention can be used as medicaments with a β$_3$ agonist action.

Thus, according to another of its aspects, a subject matter of the invention is a medicament which comprises a compound of formula (I), or an addition salt of the latter with a pharmaceutically acceptable acid, or also a hydrate or a solvate of the compound of formula (I).

Examples of diseases in which β$_3$ receptors are implicated are extensively described in the literature. The compounds of formula (I), and their pharmaceutically acceptable salts, or hydrates or solvates of these compounds, can thus be indicated for the treatment of gastrointestinal diseases, such as inflammatory diseases of the intestine, for example irritable bowel syndrome (IBS) or inflammatory bowel disease (IBD), as modulators of intestinal motricity, as lipolytics, antiobesity agents, antidiabetics, antiglaucoma agents or cicatrizants, as inhibitors of uterine contractions, as tocolytics for preventing or delaying premature labor, and for the treatment and/or prophylaxis of dysmenorrhea. In addition, the compounds of formula (I), and their pharmaceutically acceptable salts, or hydrates or solvates of these compounds, can be used in the treatment of certain diseases of the central nervous system, for example as psychotropics or antidepressants, and for certain disorders of the urinary system, such as urinary incontinence.

The present invention, according to another of its aspects, also relates to a method for the treatment of the pathologies indicated above which comprises the administration, to a patient, of an effective dose of a compound according to the invention, or one of its pharmaceutically acceptable salts, or a hydrate or solvate of this compound.

The present invention also relates to pharmaceutical compositions comprising, as active principle, at least one compound according to the invention. These pharmaceutical compositions comprise an effective dose of a compound according to the invention, or a pharmaceutically acceptable salt, a hydrate or solvate of said compound, and at least one pharmaceutically acceptable excipient.

Said excipients are chosen, according to the pharmaceutical form and the method of administration desired, from the usual excipients which are known to a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its optional salt, solvate or hydrate, can be administered in a unit administration form, as a mixture with conventional pharmaceutical excipients, to animals and to man for the prophylaxis or the treatment of the above disorders or diseases.

The appropriate unit administration forms comprise oral forms, such as tablets, soft or hard gelatin capsules, powders, granules and solutions or suspensions to be taken orally, sublingual, buccal, intratracheal, intraocular or intranasal administration forms, inhalation administration forms, topical, transdermal, subcutaneous, intramuscular or intravenous administration forms, rectal administration forms and implants. For topical application, use may be made of the compounds according to the invention in creams, gels, ointments or lotions.

The dose of active principle administered by is between 0.01 and 20 mg per kilo of body weight of the mammal to be treated, preferably between 0.1 and 10 mg/kg. In man, the dose can vary from 0.5 mg to 1500 mg per day, for example from 2.5 to 500 mg, according to the age of the subject to be treated, the type of treatment (prophylactic or curative) and the seriousness of the condition. The compounds of formula (I) are generally administered in a unit dosage form of 0.1 to 500 mg, preferably of 0.5 to 100 mg, of active principle, between one and five times daily.

There may be specific cases where higher or lower dosages are appropriate; such dosages do not depart from the scope of the invention. According to the usual practice, the dosage appropriate to each patient is determined by the physician according to the method of administration, the weight and the response of said patient.

What is claimed is:

1. A compound of formula (I)

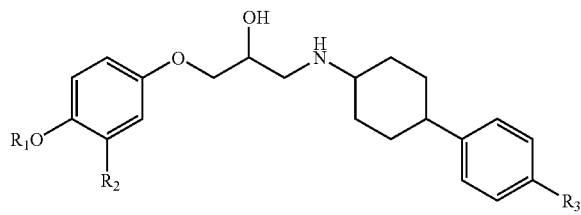

wherein:
- $R_1$ is a hydrogen atom, a $(C_1-C_4)$alkyl group, a —$CO(C_1-C_4)$alkyl group, a $(C_1-C_4)$alkylphenyl group or a —CO-phenyl group, wherein the phenyl moiety is optionally substituted by one to three groups chosen, independently of one another, from halogen atoms, $(C_1-C_4)$alkyl groups and $(C_1-C_4)$alkoxy groups;
- $R_2$ is chosen from one of the following groups:
  - a hydrogen atom,
  - a halogen atom,
  - an —$S(O)_z(C_1-C_4)$alkyl group, where z is equal to 0, 1 or 2,
  - an —$NHSO_2(C_1-C_4)$alkyl group,
  - an —$NHSO_2$-phenyl group, or
  - an —$NHSO_2$—$(C_1-C_4)$alkylphenyl group, wherein the phenyl moiety is optionally substituted by one to three groups chosen, independently of one another, from halogen atoms, $(C_1-C_4)$alkyl groups and $(C_1-C_4)$alkoxy groups; and
- $R_3$ is chosen from one of the following groups:
  - an —X—$R_4$ group, wherein X is a bond, an oxygen atom or a —$CH_2$— group and $R_4$ represents a hydrogen atom or a group of formula —$CR_5R_6$—$COOR_7$, where $R_5$, $R_6$ and $R_7$ are, independently of one another, a hydrogen atom or a $(C_1-C_4)$alkyl group, provided that $R_4$ is not a hydrogen atom when X is a bond or a —$CH_2$— group,
  - a phenyl group wherein the phenyl is optionally substituted by one to three groups chosen, independently of one another, from halogen atoms, $(C_1-C_4)$alkyl groups and $(C_1-C_4)$alkoxy groups, or is fused with a dioxolane group, or
  - a —CO—$NR_8R_9$ group, wherein $R_8$ is a hydrogen atom, a $(C_1-C_4)$alkyl group or a $(C_1-C_4)$alkylene-$(C_1-C_4)$alkoxy group and $R_9$ is chosen from one of the following groups:
    - a $(C_1-C_4)$alkylene-$(C_1-C_4)$alkoxy group,
    - a group of formula —$(CH_2)_n$-A, wherein n is equal to 0, 1, 2, 3 or 4 and A is an indolyl, fluorenyl or phenyl group, wherein the phenyl group is substituted by one to three groups independently chosen from halogen atoms, hydroxy group and $(C_1-C_4)$alkyl groups,
    - an —NH-phenyl group, wherein the phenyl group is optionally substituted by one to three groups chosen, independently of one another, from halogen atoms, hydroxy group and ($C_1$-$C_4$)alkyl groups, or a group of formula —CH($R_{10}$)—($CH_2$)$_n$—COOR$_{11}$, wherein n is equal to 0, 1, 2 or 3, $R_{11}$ is a hydrogen atom or a ($C_1$-$C_4$)alkyl group and $R_{10}$ is:
a hydrogen atom,
a ($C_1$-$C_4$)alkyl group,
a —COOR$_{12}$ group, wherein $R_{12}$ is a hydrogen atom or a ($C_1$-$C_4$)alkyl group, or
a —$CH_2$-phenyl group, wherein the phenyl group is optionally substituted by one to three groups chosen, independently of one another, from halogen atoms, hydroxy group and ($C_1$-$C_4$)alkyl groups; or a salt, hydrate or solvate thereof.

2. The compound according to claim 1 wherein $R_1$ is a hydrogen atom,
or a salt, hydrate or solvate thereof.

3. The compound according to claim 1 wherein $R_2$ is an —$SO_2$($C_1$-$C_4$)alkyl group or an —$NHSO_2$($C_1$-$C_4$)alkyl group,
or a salt, hydrate or solvate thereof.

4. The compound according to claim 1 wherein $R_3$ is chosen from one of the following groups:
an —X—$R_4$ group, wherein X and $R_4$ are as defined in claim 1, provided that $R_4$ is not a hydrogen atom when X is a bond or a —$CH_2$— group,
a phenyl group wherein the phenyl is optionally substituted by one to three groups chosen, independently of one another, from halogen atoms, ($C_1$-$C_4$)alkyl groups and ($C_1$-$C_4$)alkoxy groups, or is fused with a dioxolane group, or
a —CO—NR$_8$R$_9$ group, wherein $R_8$ and $R_9$ are as defined in claim 1;
or a salt, hydrate or solvate thereof.

5. The compound according to claim 4 wherein $R_3$ is a —CO—NHR$_9$ group, wherein $R_9$ is chosen from one of the following groups:
a group of formula —($CH_2$)$_n$-A, wherein n is equal to 0, 1, 2, 3 or 4 and A is an indolyl group, a fluorenyl group or a phenyl group, wherein the phenyl group is substituted by one to three groups independently chosen from halogen atoms, hydroxy group and ($C_1$-$C_4$)alkyl groups,
an —NH-phenyl group, wherein the phenyl group is optionally substituted by one to three groups chosen, independently of one another, from halogen atoms, hydroxy group and ($C_1$-$C_4$)alkyl groups, or
a group of formula —CH($R_{10}$)—($CH_2$)$_n$—COOR$_{11}$, wherein n is equal to 0, 1, 2 or 3, $R_{11}$ is a hydrogen atom or a ($C_1$-$C_4$)alkyl group and $R_{10}$ is:
a hydrogen atom,
a ($C_1$-$C_4$)alkyl group,
a —COOR$_{12}$ group, wherein $R_{12}$ is a hydrogen atom or a ($C_1$-$C_4$)alkyl group, or
a —$CH_2$-phenyl group, wherein the phenyl group is optionally substituted by one to three groups chosen, independently of one another, from halogen atoms, hydroxy group and ($C_1$-$C_4$)alkyl groups;
or a salt, hydrate or solvate thereof.

6. A process for preparing the compound according to claim 1 wherein $R_3$ is other than a —CO—NR$_8$R$_9$ group, comprising reacting a compound of formula (II), wherein R is an electrophilic group and Pg is a protective group, with an epoxide of formula (III), wherein, $R_1$ and $R_2$ are as defined in claim 1:

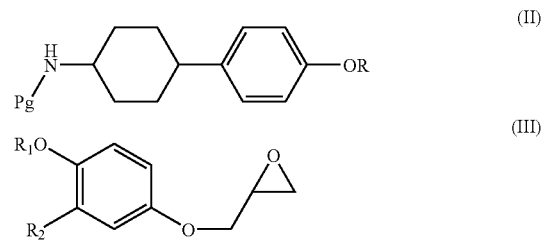

to obtain a compound of formula (IV):

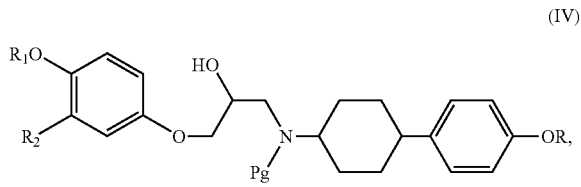

converting the compound of formula (IV) into a compound of formula (V), wherein $R_3$ is as defined in claim 1 but is other than a —CO—NR$_8$R$_9$ group:

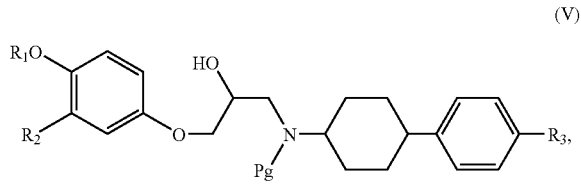

and deprotecting the compound of formula (V).

7. A process for preparing the compound according to claim 1 wherein $R_3$ is a —CO—NR$_8$R$_9$ group, comprising reacting a compound of formula (XII):

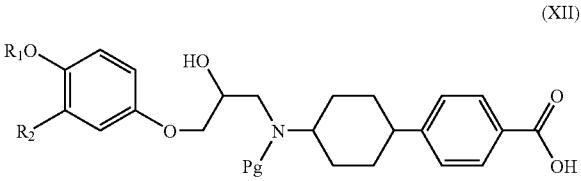

where $R_1$ and $R_2$ are as defined in claim 1 and Pg is a protective group with an amine of formula HNR$_8$R$_9$, wherein $R_8$ and $R_9$ are as defined in claim 1, and then the protective group from the product thus obtained.

8. A pharmaceutical composition comprising the compound according to claim 1 or a salt, hydrate or solvate thereof, and at least one pharmaceutically acceptable excipient.

9. A method for treating a diseases in which $\beta_3$ receptor is implicated comprising administering to a patient in need thereof an effective amount of the compound according to claim 1 or a salt, hydrate or solvate thereof.

10. The method according to claim 9 for treating a gastrointestinal disease, an inflammatory disease of the intestine, irritable bowel syndrome (IBS), inflammatory bowel disease (IBD), obesity, diabeties, glaucoma, dysmenorrheal, depression, or urinary incontinence for modulating intestinal motricity, for causing lipolysis or cicatrizing, for inhibiting uterine contraction, or for preventing or delaying premature labor.

11. The compound according to claim 2 wherein $R_2$ is an $—SO_2(C_1-C_4)$alkyl group or an $—NHSO_2(C_1-C_4)$alkyl group, or a salt, hydrate or solvate thereof.

12. The compound according to claim 2 wherein $R_3$ is chosen from one of the following groups:

an $—X—R_4$ group, wherein X is a bond, an oxygen atom or a $—CH_2—$ group and $R_4$ represents a hydrogen atom or a group of formula $—CR_5R_6—COOR_7$, where $R_5$, $R_6$ and $R_7$ are, independently of one another, a hydrogen atom or a $(C_1-C_4)$alkyl group, provided that $R_4$ is not a hydrogen atom when X is a bond or a $—CH_2—$ group, a phenyl group wherein the phenyl is optionally substituted by one to three groups chosen, independently of one another, from halogen atoms, $(C_1-C_4)$alkyl groups and $(C_1-C_4)$alkoxy groups, or is fused with a dioxolane group, or a $—CO—NR_8R_9$ group, wherein $R_8$ is a hydrogen atom, a $(C_1-C_4)$alkyl group or a $(C_1-C_4)$alkylene-$(C_1-C_4)$alkoxy group and $R_9$ is chosen from one of the following groups:

a $(C_1-C_4)$alkylene-$(C_1-C_4)$alkoxy group, a group of formula $—(CH_2)_n$-A, wherein n is equal to 0, 1, 2, 3 or 4 and A is an indolyl group, a fluorenyl group or a phenyl group, wherein the phenyl group is substituted by one to three groups independently chosen from halogen atoms, hydroxy group and $(C_1$-C4$)$alkyl groups, an $—NH$-phenyl group, wherein, the phenyl group is optionally substituted by one to three groups chosen, independently of one another, from halogen atoms, hydroxy group and $(C_1-C_4)$alkyl groups, or a group of formula $—CH(R_{10})—(CH_2)_n—COOR_{11}$, where n is equal to 0, 1, 2 or 3, $R_{11}$ is a hydrogen atom or a $(C_1-C_4)$alkyl group and $R_{10}$ is:

a hydrogen atom, a $(C_1-C_4)$alkyl group, a $—COOR_{12}$ group, wherein $R_{12}$, is a hydrogen atom or a $(C_1-C_4)$alkyl group, or a $—CH_2$-phenyl group, wherein the phenyl group is optionally substituted by one to three groups chosen, independently of one another, from halogen atoms, hydroxy group and $(C_1-C_4)$alkyl groups;

or a salt, hydrate or solvate thereof.

13. The compound according to claim 3 wherein $R_3$ is chosen from one of the following groups:

an $—X—R_4$ group, wherein X is a bond, an oxygen atom or a $—CH_2—$ group and $R_4$ represents a hydrogen atom or a group of formula $—CR_5R_6—COOR_7$, where $R_5$, $R_6$ and $R_7$ are, independently of one another, a hydrogen atom or a $(C_1-C_4)$alkyl group, provided that $R_4$ is not a hydrogen atom when X is a bond or a $—CH_2—$ group, a phenyl group wherein the phenyl is optionally substituted by one to three groups chosen, independently of one another, from halogen atoms, $(C_1-C_4)$alkyl groups and $(C_1-C_4)$alkoxy groups, or is fused with a dioxolane group, or a $—CO—NR_8R_9$ group, wherein $R_8$ is a hydrogen atom, a $(C_1-C_4)$alkyl group or a $(C_1-C_4)$alkylene-$(C_1-C_4)$alkoxy group and $R_9$ is chosen from one of the following groups:

a $(C_1-C_4)$alkylene-$(C_1-C_4)$alkoxy group, a group of formula $—(CH_2)_n$-A, wherein n is equal to 0, 1, 2, 3 or 4 and A is an indolyl group, a fluorenyl group or a phenyl group, wherein the phenyl group is substituted by one to three groups independently chosen from halogen atoms, hydroxy group and $(C_1-C_4)$alkyl groups, an $—NH$-phenyl group, wherein the phenyl group is optionally substituted by one to three groups chosen, independently of one another, from halogen atoms, hydroxy group and $(C_1-C_4)$alkyl groups, or a group of formula $—CH(R_{10})—(CH_2)_n—COOR_{11}$, where n is equal to 0, 1, 2 or 3, $R_{11}$ is a hydrogen atom or a $(C_1-C_4)$alkyl group and $R_{10}$ is:

a hydrogen atom, a $(C_1-C_4)$alkyl group, a $—COOR_{12}$ group, wherein $R_{12}$ is a hydrogen atom or a $(C_1-C_4)$alkyl group, or a $—CH_2$-phenyl group, wherein the phenyl group is optionally substituted by one to three groups chosen, independently of one another, from halogen atoms, hydroxy group and $(C_1-C_4)$alkyl groups;

or a salt, hydrate or solvate thereof.

14. A pharmaceutical composition comprising the compound according to claim 2 or salt, hydrate or solvate thereof, and at least one pharmaceutically acceptable excipient.

15. A pharmaceutical composition comprising the compound according to claim 3 or a salt, hydrate or solvate thereof, and at least one pharmaceutically acceptable excipient.

16. A pharmaceutical composition comprising the compound according to claim 4 or a salt, hydrate or solvate thereof, and at least one pharmaceutically acceptable excipient.

17. A pharmaceutical composition comprising the compound according to claim 5 or a salt, hydrate or solvate thereof, and at least one pharmaceutically acceptable excipient.

18. A pharmaceutical composition comprising the compound according to claim 11 or a salt, hydrate or solvate thereof, and at least one pharmaceutically acceptable excipient.

19. A pharmaceutical composition comprising the compound according to claim 12 or a salt, hydrate or solvate thereof, and at least one pharmaceutically acceptable excipient.

20. A pharmaceutical composition comprising the compound according to claim 13 or a salt, hydrate or solvate thereof, and at least one pharmaceutically acceptable excipient.

21. A method for treating a disease in which $\beta_3$ receptor is implicated comprising administering to a patient in need thereof an effective amount of the compound according to claim 2 or a salt, hydrate or solvate thereof.

22. A method for treating a disease in which $\beta_3$ receptor is implicated comprising administering to a patient in need thereof an effective amount of the compound according to claim 3 or a salt, hydrate or solvate thereof.

23. A method for treating a disease in which $\beta_3$ receptor is implicated comprising administering to a patient in need thereof an effective amount of the compound according to claim 4 or a salt, hydrate or solvate thereof.

24. A method for treating a disease in which $\beta_3$ receptor is implicated comprising administering to a patient in need thereof an effective amount of the compound according to claim 5 or a salt, hydrate or solvate thereof.

25. A method for treating a disease in which $\beta_3$ receptor is implicated comprising administering to a patient in need thereof an effective amount of the compound according to claim 11 or a salt, hydrate or solvate thereof.

26. A method for treating a disease in which $\beta_3$ receptor is implicated comprising administering to a patient in need thereof an effective amount of the compound according to claim 12 or a salt, hydrate or solvate thereof.

27. A method for treating a disease in which $\beta_3$ receptor is implicated comprising administering to a patient in need thereof an effective amount of the compound according to claim 13 or a salt, hydrate or solvate thereof.

28. The method according to claim 21 for treating a gastrointestinal diseases, an inflammatory disease of the intestine, irritable bowel syndrome (IBS), inflammatory bowel disease (IBD), obesity, diabeties, glaucoma, dysmenorrheal, depression, or urinary incontinence for modulating intestinal motricity, for causing lipolysis or cicatrizing, for inhibiting uterine contraction, or for preventing or delaying premature labor.

29. The method according to claim 22 for treating a gastrointestinal diseases, an inflammatory disease of the intestine, irritable bowel syndrome (IBS), inflammatory bowel disease (IBD), obesity, diabeties, glaucoma, dysmenorrheal, depression, or urinary incontinence for modulating intestinal motricity, for causing lipolysis or cicatrizing, for inhibiting uterine contraction, or for preventing or delaying premature labor.

30. The method according to claim 23 for treating a gastrointestinal diseases, an inflammatory disease of the intestine, irritable bowel syndrome (IBS), inflammatory bowel disease (IBD), obesity, diabeties, glaucoma, dysmenorrheal, depression, or urinary incontinence for modulating intestinal motricity, for causing lipolysis or cicatrizing, for inhibiting uterine contraction, or for preventing or delaying premature labor.

31. The method according to claim 24 for treating a gastrointestinal diseases, an inflammatory disease of the intestine, irritable bowel syndrome (IBS), inflammatory bowel disease (IBD), obesity, diabeties, glaucoma, dysmenorrheal, depression, or urinary incontinence for modulating intestinal motricity, for causing lipolysis or cicatrizing, for inhibiting uterine contraction, or for preventing or delaying premature labor.

32. The method according to claim 25 for treating a gastrointestinal diseases, an inflammatory disease of the intestine, irritable bowel syndrome (IBS), inflammatory bowel disease (IBD), obesity, diabeties, glaucoma, dysmenorrheal, depression, or urinary incontinence for modulating intestinal motricity, for causing lipolysis or cicatrizing, for inhibiting uterine contraction, or for preventing or delaying premature labor.

33. The method according to claim 26 for treating a gastrointestinal diseases, an inflammatory disease of the intestine, irritable bowel syndrome (IBS), inflammatory bowel disease (IBD), obesity, diabeties, glaucoma, dysmenorrheal, depression, or urinary incontinence for modulating intestinal motricity, for causing lipolysis or cicatrizing, for inhibiting uterine contraction, or for preventing or delaying premature labor.

34. The method according to claim 27 for treating a gastrointestinal diseases, an inflammatory disease of the intestine, irritable bowel syndrome (IBS), inflammatory bowel disease (IBD), obesity, diabeties, glaucoma, dysmenorrheal, depression, or urinary incontinence for modulating intestinal motricity, for causing lipolysis or cicatrizing, for inhibiting uterine contraction, or for preventing or delaying premature labor.

* * * * *